United States Patent
Gonda

(10) Patent No.: US 8,620,399 B2
(45) Date of Patent: Dec. 31, 2013

(54) DEFLECTABLE MEDICAL DEVICES AND METHODS OF MANUFACTURING THEREFOR

(75) Inventor: Edward Gonda, Minneapolis, MN (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 281 days.

(21) Appl. No.: 12/982,191

(22) Filed: Dec. 30, 2010

(65) Prior Publication Data

US 2012/0172717 A1 Jul. 5, 2012

(51) Int. Cl.
*A61B 5/042* (2006.01)
*A61B 18/14* (2006.01)
*A61N 1/05* (2006.01)

(52) U.S. Cl.
USPC ............ 600/372; 600/509; 606/41; 607/116; 29/825

(58) Field of Classification Search
USPC ............ 600/373, 509; 606/41; 607/116, 119; 29/825; 128/898
See application file for complete search history.

(56) References Cited

U.S. PATENT DOCUMENTS

| | | | | |
|---|---|---|---|---|
| 4,630,611 A * | 12/1986 | King | ............................. | 600/377 |
| 4,934,340 A * | 6/1990 | Ebling et al. | .................... | 600/151 |
| 5,063,018 A * | 11/1991 | Fontirroche et al. | .......... | 264/514 |
| 5,201,903 A * | 4/1993 | Corbett et al. | .................. | 29/872 |
| 5,417,208 A * | 5/1995 | Winkler | ........................ | 600/374 |
| 5,476,495 A * | 12/1995 | Kordis et al. | .................. | 607/122 |
| 5,499,981 A * | 3/1996 | Kordis | ............................. | 606/41 |
| 5,591,142 A * | 1/1997 | Van Erp | ......................... | 604/526 |
| 5,662,606 A * | 9/1997 | Cimino et al. | .............. | 604/95.04 |
| 5,843,031 A | 12/1998 | Hermann et al. | | |
| 6,952,616 B2 * | 10/2005 | Wessman et al. | ............. | 607/122 |
| 7,669,309 B2 | 3/2010 | Johnson et al. | | |
| 7,706,891 B2 | 4/2010 | Hastings et al. | | |
| 7,824,517 B2 | 11/2010 | Kampa et al. | | |
| 8,147,486 B2 * | 4/2012 | Honour et al. | ................... | 606/41 |
| 2002/0038139 A1 * | 3/2002 | Wessman et al. | ............. | 607/122 |
| 2002/0095074 A1 * | 7/2002 | Al-Ali | ........................... | 600/310 |
| 2003/0050680 A1 * | 3/2003 | Gibson et al. | ................. | 607/116 |
| 2003/0092303 A1 * | 5/2003 | Osypka | ........................ | 439/274 |
| 2004/0220461 A1 | 11/2004 | Schwartz | | |
| 2005/0027341 A1 * | 2/2005 | Schrom et al. | ................. | 607/116 |
| 2007/0282411 A1 * | 12/2007 | Franz et al. | .................... | 607/116 |
| 2007/0299424 A1 | 12/2007 | Cumming et al. | | |
| 2009/0248122 A1 * | 10/2009 | Pianca | .......................... | 607/115 |
| 2010/0059173 A1 * | 3/2010 | Kampa et al. | ............. | 156/244.15 |
| 2010/0211147 A1 * | 8/2010 | Schiefer et al. | ............... | 607/116 |
| 2012/0130217 A1 * | 5/2012 | Kauphusman et al. | ........ | 600/373 |

* cited by examiner

*Primary Examiner* — Lee S Cohen
*Assistant Examiner* — Erin M Cardinal
(74) *Attorney, Agent, or Firm* — Dykema Gossett PLLC

(57) ABSTRACT

Medical devices, methods of manufacturing medical devices, and systems comprising medical devices are provided. The medical device comprises a shaft having a proximal end, a distal end, and a major lumen disposed therein extending between the proximal end and the distal end. The major lumen is configured to receive a second medical device therein. The shaft comprises an inner liner, a generally planar element wrapped in a spiral pattern about the outer surface of the inner liner, and an outer layer. The generally planar element has a longitudinal axis and a plurality of longitudinally extending ribs and comprises a polymeric material.

15 Claims, 13 Drawing Sheets

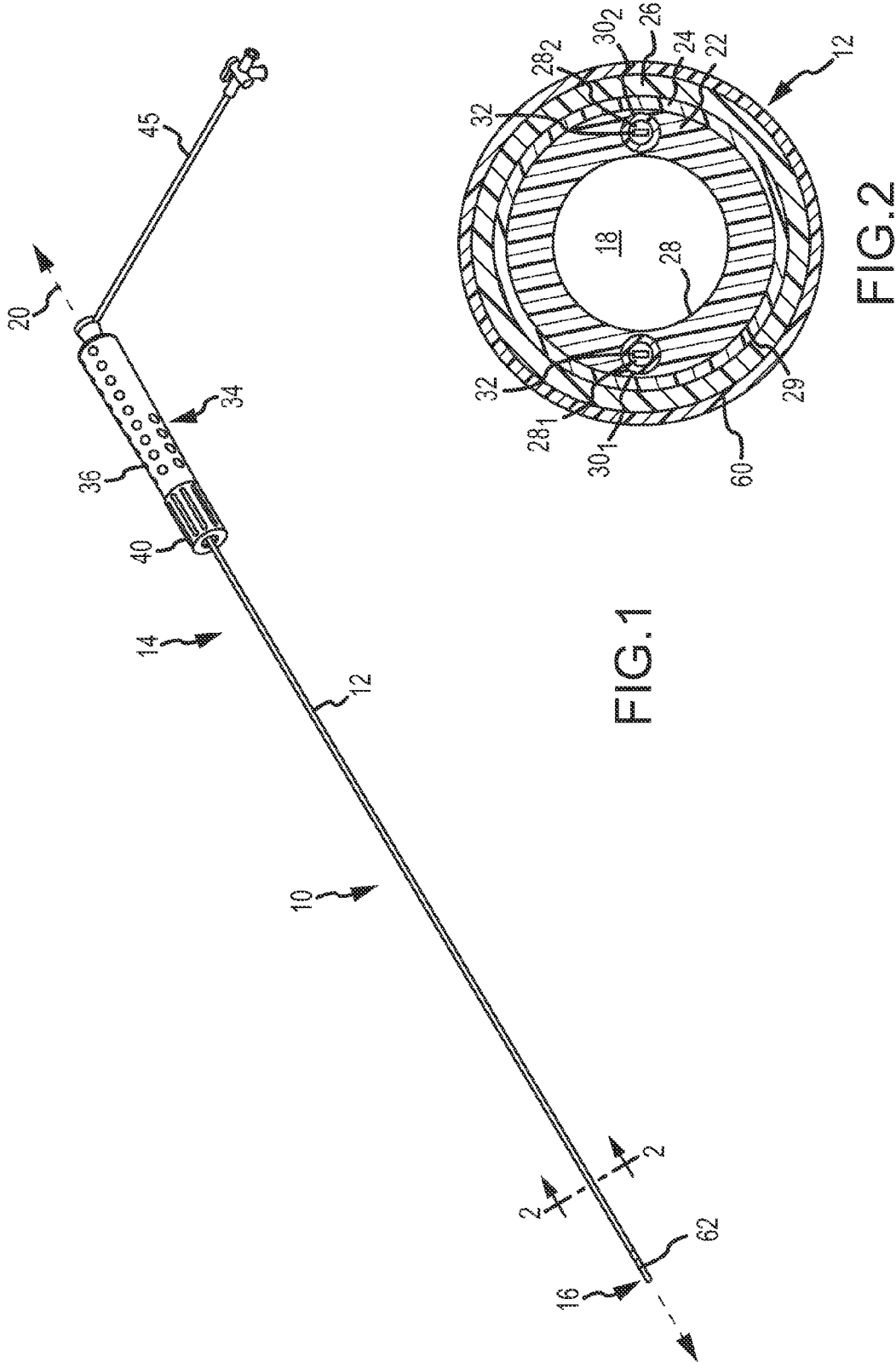

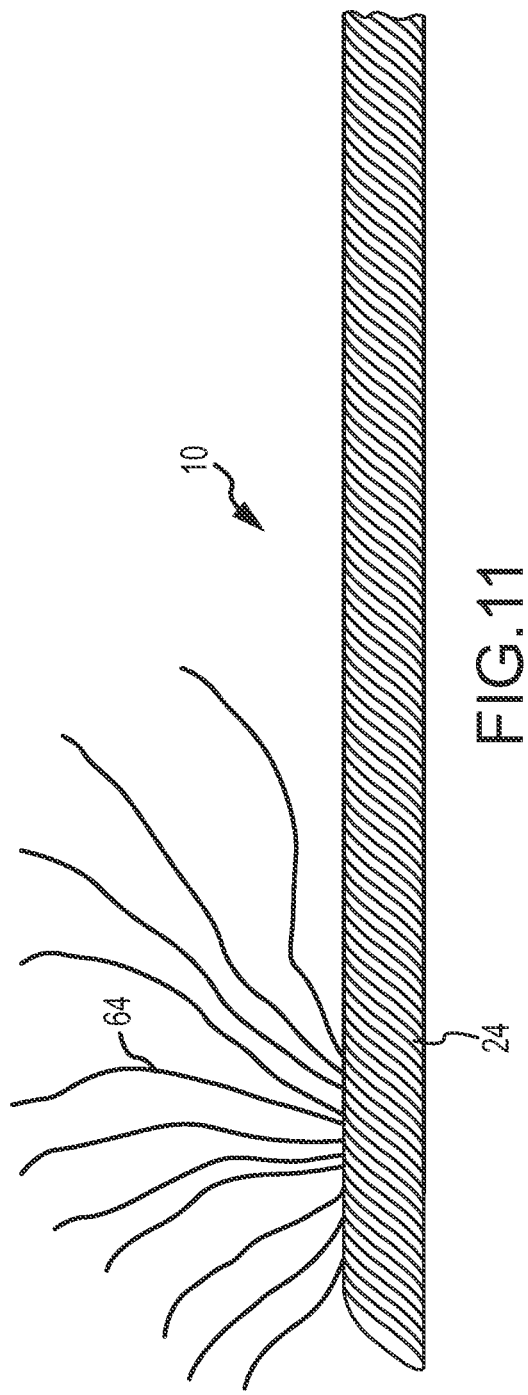
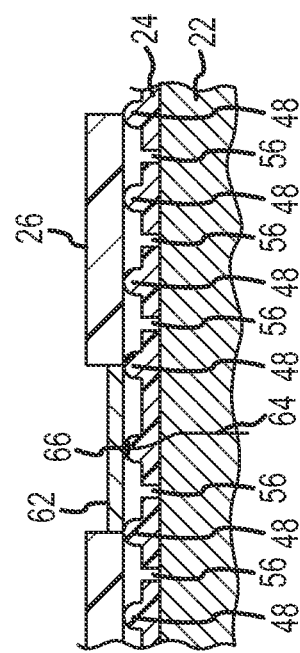

DEFLECTABLE MEDICAL DEVICES AND METHODS OF MANUFACTURING THEREFOR

BACKGROUND OF THE INVENTION a. Field of the Invention

The instant disclosure relates generally to a family of medical devices. More particularly, the instant disclosure relates to medical devices, such as, for example, deflectable sheaths or catheter-introducers, having a generally planar element wrapped in spiral pattern about the sheath or catheter-introducer, where the generally planar element comprises a polymeric material. The instant disclosure further relates to deflectable sheaths or catheter-introducers having a generally planar element wrapped in a spiral pattern about the catheter-introducer or sheath wherein the generally planar element has a longitudinal axis and a plurality of longitudinally extending ribs. The instant disclosure further relates to methods of manufacturing such medical devices and systems with which such medical devices are used.

b. Background Art

Electrophysiology catheters are used in a variety of diagnostic and/or therapeutic medical procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

A medical procedure in which an electrophysiology catheter is used includes a first diagnostic catheter deployed through a patient's vasculature to a patient's heart or a chamber or vein thereof. An electrophysiology catheter that carries one or more electrodes can be used for cardiac mapping or diagnosis, ablation and/or other therapy delivery modes, or both. Once at the intended site, treatment can include radio frequency (RF) ablation, cryoablation, laser ablation, chemical ablation, high-intensity focused ultrasound-based ablation, microwave ablation, etc. An electrophysiology catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents stray errant conduction signals that can form the basis for arrhythmias.

It is well known to use a medical device called a sheath or catheter-introducer when performing various therapeutic and/or diagnostic medical procedures on or in the heart, for example. Once inserted into a patient's body, these particular medical devices (hereinafter referred to as "sheaths") provide a path through a patient's vasculature to a desired anatomical structure or site for a second medical device, such as, for example, a catheter, a needle, a dilator, etc., and also allow for the proper positioning or placement of the second medical device relative to the desired anatomical structure.

To increase the ability to move and navigate a sheath within a patient's body, steerable sheaths have been designed. Steerable sheaths are often manipulated by selectively tensioning one or more pull wires running along the length of the sheath, typically offset from a central longitudinal axis of the sheath, thereby deflecting the distal end of the sheath in one or more planes. Pull wires (or other deflectable elements) can be disposed within lumens formed by tubes (i.e., so-called spaghetti tubes) that are manually bonded to an inner liner of the sheath. While commercially and functionally acceptable, the step of manually bonding the spaghetti tubes to an inner liner of the sheath increases the time and expense associated with manufacturing of the sheaths.

In addition, a sheath can include an optional braided wire assembly designed to reinforce the sheath and to transmit torque along the length of the sheath. The braided wire assembly can be formed of a metal such as stainless steel and can be formed in various braid patterns and densities. While commercially and functionally acceptable, a braided wire assembly can require manual processing of the braided assembly during assembly of the sheath (e.g., hand-stretching of the braided assembly).

Moreover, visualization of a sheath and/or its position has proved difficult. As a result, physicians have been unable to see the sheath and/or its position during the performance of a medical procedure without the use of ionizing radiation (e.g., acute x-ray delivery via a fluoroscope). However, with the advent and growing use of various automated guidance systems, such as, for example magnetic-based and robotic-based guidance systems, the need for such visualization capability has increased. More particularly, it is important for the physician/clinician operating such automated systems to know and understand exactly where the various medical devices being used are located and/or how they are positioned. In addition to the need for visualization in the use of automated guidance systems, the need for this capability also exists in certain instances where a physician manually controls medical devices. For example, the transseptal crossing point for procedures performed on the left side of a heart is not readily visible using fluoroscopy.

BRIEF SUMMARY OF THE INVENTION

It is desirable to be able to provide sheaths that have improved manufacturability. In particular, it can be desirable to reduce and/or eliminate manual processing of the components of the sheath during manufacturing. In addition, it can be desirable to improve visualization of a sheath and/or its position through the use of electrodes mounted on the sheath without significantly complicating the manufacturing process.

The instant disclosure relates to a family of medical device, such as deflectable sheaths and catheter-introducers. These medical devices typically comprise a shaft having a proximal end, a distal end, and a major lumen disposed therein extending between the proximal end and the distal end and configured to receive a second medical device therein.

In an exemplary embodiment, the shaft of the medical device is formed of a number of constituent parts. The shaft includes an inner liner having an inner surface and an outer surface, wherein the inner surface of the inner liner forms or defines the major lumen of the shaft. The inner liner can comprise polytetrafluoroethylene (PTFE). The inner liner has a plurality of minor lumens disposed therein. Means for deflecting the shaft in at least one direction relative to a longitudinal axis of the shaft are at least partially disposed within at least one of the plurality of minor lumens.

The shaft further includes a generally planar element wrapped in a spiral pattern about the outer surface of the inner liner, wherein the generally planar element has a longitudinal axis and a plurality of longitudinally extending ribs. Each of the ribs has a corresponding lumen disposed therein. The generally planar element comprises a polymeric material. The polymeric material of the generally planar element can comprise polyether ether ketone (PEEK), nylon, PTFE, or a combination thereof.

The shaft further includes an outer layer comprising a polymeric material, wherein at least a portion of the outer layer is adjacent the outer surface of the inner liner. The polymeric material of the outer layer comprises nylon or polyether block amides or combinations thereof.

In accordance with an aspect of the disclosure, the medical device can further include an electrode mounted on the shaft. An electrical wire connected to the electrode can be disposed within a corresponding lumen of one of the plurality of ribs of the generally planar element in an embodiment. The corresponding lumen of one of the plurality of ribs extending at least from the proximal end of the shaft to a location on the shaft near where the electrode is mounted. The electrical wire connected to the electrode can also be disposed within one of the plurality of ribs (e.g., within a wall) of the generally planar element in accordance with another embodiment.

In accordance with another aspect of the disclosure, a method of manufacturing a medical device is provided. The method, in accordance with present teachings, includes forming a shaft of the medical device by forming an inner liner having a tubular shape and an inner tubular surface and an outer tubular surface; wrapping a generally planar element in a spiral pattern about the outer tubular surface of the inner liner, wherein the generally planar element has a longitudinal axis and a plurality of longitudinally extending ribs (each having a corresponding lumen disposed therein) and comprises a polymeric material; forming an outer layer by covering the inner liner with a polymeric material; heating the shaft to a predetermined temperature at which the polymeric material of the outer layer melts; and cooling the shaft. The inner liner can be formed by extruding the inner liner over a mandrel; coextruding a plurality of polymeric tubes within the inner liner, wherein each of the plurality of polymeric tubes defines a minor lumen disposed in the inner liner; and selectively removing at least a portion of each of the polymeric tubes. The method can further include the substep of selectively removing at least a portion of the generally planar element.

In embodiments where the medical device includes an electrode, the method can further include the step of mounting an electrode onto the shaft prior to the step of forming an outer layer. In some embodiments, the method can further include the steps of providing an electrical wire within the corresponding lumen of one of the plurality of ribs of the generally planar element prior to the step of forming an outer layer, wherein the corresponding lumen of at least one of the plurality of ribs extends at least from the proximal end of the shaft to a location on the shaft near where the electrode is mounted; and creating an opening in the generally planar element through which the electrical wire extends to connect the electrical wire to the electrode. In other embodiments, the method can further include the steps of providing an electrical wire within at least one of the plurality of ribs of the generally planar element (e.g., within a wall of the rib) prior to the step of forming an outer layer and creating an opening in the generally planar element through which the electrical wire extends to connect the electrical wire to the electrode.

In accordance with yet another aspect of the disclosure, a system for performing at least one of a therapeutic and diagnostic medical procedure is provided. In accordance with the present disclosure, the system comprises a first medical device having an elongate shaft and at least one electrode mounted on the shaft. The shaft of the medical device comprises a proximal end, a distal end, and a major lumen extending between the proximal end and the distal end of the shaft. The major lumen is sized and configured to receive a second medical device (for example and without limitation, an electrophysiological catheter, a needle, a dilator, and/or the like) therein. The shaft of the first medical device includes: an inner liner having an inner surface and an outer surface, the inner surface forming the major lumen; a generally planar element having a longitudinal axis and having a plurality of longitudinally extending ribs, wherein the generally planar element comprises a polymeric material and is wrapped in a spiral pattern about the outer surface of the inner liner and wherein each of the ribs has a corresponding lumen disposed therein in which an electrical wire connected to the electrode is disposed; and an outer layer comprising a polymeric material, wherein at least a portion of the outer layer is adjacent the outer surface of the inner liner. The system further comprises an electronic control unit (ECU). The ECU is configured to receive signals from the electrode mounted on the shaft of the medical device and, in response to the received signals, to automatically determine a position of the electrode and/or monitor electrophysiological data.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 1 is a perspective view of an exemplary embodiment of a medical device in accordance with present teachings.

FIG. 2 is a cross-sectional view of the medical device illustrated in FIG. 1 taken along the line 2-2 showing the shaft of the medical device.

FIG. 11 is a side view of a portion of the medical device of FIG. 1 with a plurality of electrical conductors or wires exposed.

FIG. 12 is a schematic partial side sectional view of a portion of the medical device of FIG. 1 with an electrode mounted thereon.

DETAILED DESCRIPTION OF THE DISCLOSURE

Figure 3:
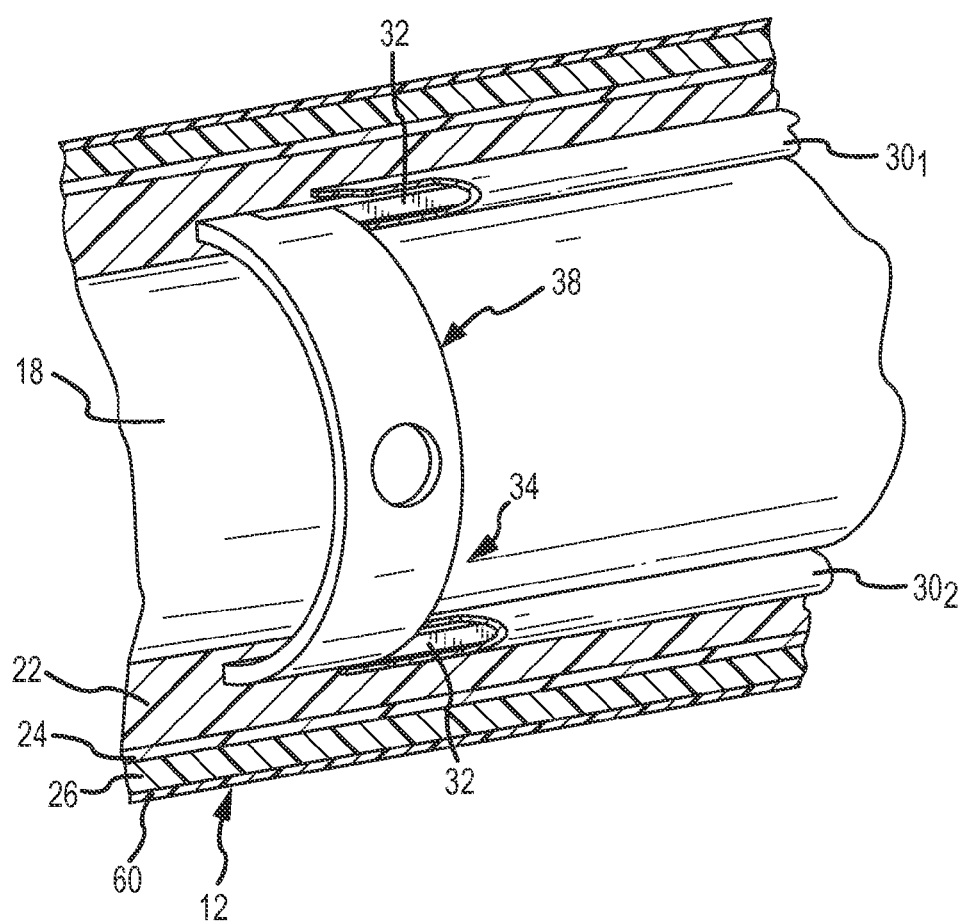
FIG. 3 is a cut-away perspective view of a portion of the medical device of FIG. 1.

The instant disclosure generally relates to deflectable medical devices. For purposes of this description, similar aspects among the various embodiments described herein will be referred to by the same reference number. As will be appreciated, however, the structure of the various aspects can be different among the various embodiments. FIG. 1 generally illustrates one exemplary embodiment of a deflectable medical device 10, such as, for example and without limitation, a sheath or catheter-introducer for use in connection with any number of diagnostic and therapeutic procedures performed, for example, within the heart of a human being or an animal. For purposes of clarity and brevity, the description below will be directed solely to a deflectable medical device 10 that comprises a sheath (i.e., sheath 10) for use in cardiac applications. However, it will be appreciated by those having ordinary skill in the art that the description below can be equally applicable to medical devices other than sheaths and/or for medical devices used in connection with applications other than cardiac applications. Accordingly, medical devices other than sheaths and/or medical devices for use in applications other than cardiac applications, remain within the spirit and scope of the present disclosure.

With reference to FIG. 1, in an exemplary embodiment, the sheath 10 comprises an elongate tubular shaft 12. The shaft 12 can have a straight configuration, or alternatively, can have a fixed curve shape and/or configuration. The shaft 12 is configured for insertion into a blood vessel or other anatomic structure. The shaft 12 has a proximal end 14, a distal end 16, and a major lumen 18 (best shown in FIG. 2) extending between the proximal end 14 an the distal end 16. The shaft 12 can be approximately 71 cm in length from proximal end 14 to distal end 16 in accordance with an embodiment of the disclosure. The shaft 12 can have an inside diameter that is approximately 8.5 French and an outside diameter that is approximately 11.5 French in accordance with an embodiment of the disclosure. Although these exemplary dimensions are mentioned in detail for the shaft 12, the various dimensions for the shaft 12 can vary in accordance with different embodiments of the disclosure. As used herein, "proximal" generally refers to a direction toward the end of the sheath 10 near the physician/clinician, and "distal" generally refers to a direction away from the physician/clinician. The major lumen 18 defines a longitudinal axis 20 of the sheath 10, and the major lumen 18 is configured in size and/or shape to receive a medical device therein.

FIG. 2 is a cross-sectional view of an exemplary embodiment of the shaft 12. FIG. 2 generally illustrates the shaft 12 at both a non-final stage of assembly and at a final stage of assembly following the performance of a reflow process on at least a portion of the shaft. In this embodiment, and in its most general form, the shaft 12 comprises an inner liner 22, a generally planar element 24 wrapped in a spiral pattern on the inner liner 22, and an outer layer 26.

The inner liner 22 has an inner surface 28 and an outer surface 29. The inner surface 28 defines the major lumen 18. In an exemplary embodiment, the inner liner 22 is formed of an extruded tube. The tube can be extruded over a mandrel. The mandrel can have a desired radial cross-sectional shape in view of the sheath to be made and can have a desired length in view of the sheath to be made. The extruded tube for the inner liner 22 can be constructed from a material such as PTFE, which is commonly sold by the E. I. du Pont de Nemours and Company under the trade name TEFLON®. In an exemplary embodiment, the PTFE comprises etched PTFE. An inner liner 22 formed of this particular material creates a lubricious lumen (i.e., lumen 18) within which other medical devices used with the sheath 10, such as, for example, catheters, needles, dilators, and the like, can be passed. The inner liner 22 is relatively thin. For example, in one embodiment, the inner liner 22 has a thickness on the order of 0.0015 inches (0.0381 mm). It will be appreciated by those having ordinary skill in the art that the inner liner 22 can be formed of a material other than PTFE, or etched PTFE. For example, in other exemplary embodiments, the inner liner 22 is comprised of polymeric materials, such as, for example and without limitation, polyether block amides, nylon, and other thermoplastic elastomers, or combinations thereof. Accordingly, sheaths having inner liners 22 made of materials other than PTFE remain within the spirit and scope of the disclosure.

The inner liner 22 has one or more minor lumens (i.e., minor lumens $28_1$, $28_2$ in FIG. 2) therein. The minor lumens $28_1$, $28_2$ are defined by tubes 30 (i.e. tubes 30$_1$, 30$_2$, respectively). In other words, each tube 30 (i.e. tubes 30$_1$, 30$_2$) define a corresponding minor lumen $28_1$, $28_2$. Tubes 30 can also be known as "spaghetti tubes." Tubes 30 can be formed of any number of materials known in the art, such as for example and without limitation PTFE. Tubes 30 are coextruded with the inner liner 22. By coextruding tubes 30 with the inner liner 22, additional processing steps, such as for example, manually affixing or bonding tubes 30 to another components of sheath 10 can be eliminated. Tubes 30$_1$, 30$_2$ are disposed approximately 180° apart from each other around the circumference of the inner liner 22. The minor lumens $28_1$, $28_2$ defined by tubes 30 are configured to receive and house at least a portion of a means 32 for deflecting the shaft 12 in at least one direction relative to the longitudinal axis 20 of the shaft 12. The minor lumens $28_1$, $28_2$ extend axially relative to the longitudinal axis 20 of the shaft 12. Some or all of the minor lumens $28_1$, $28_2$ extend from the proximal end 14 of the shaft 12 to the distal end 16 or from the proximal end 14 of the shaft 12 to various points or locations on the shaft 12 between the proximal and distal ends 14, 16. For example and without limitation, the minor lumens $28_1$, $28_2$ can extend from the proximal end 14 to a point in the shaft 12 where the means 32 for deflecting the shaft 12 is coupled to another components of the steering mechanism. For ease of manufacturing, the tubes 30 can extend from the proximal end 14 to the distal end 16 of the shaft 12 during coextrusion with inner liner 22. A laser process can then be utilized to remove a portion of the tubes 30 at the distal end 16 of the shaft 12. In particular, a laser process can remove a length of tubes 30 that is approximately 3 inches at the distal end 16 of the shaft 12. The lasing of a portion of the tubes 30 at the distal end 16 of the shaft 12 allows an anchoring structure 38 (as described in more detail below) to be located more proximally on the shaft 12, thereby allowing the distal end of the shaft 12 to be exposed for bonding of a tip.

Means 32 for deflecting the shaft 12 in at least one direction relative to the longitudinal axis 20 of the shaft 12 can be provided for steering of the sheath 10. In one exemplary embodiment, the movement of the sheath 10 can be controlled and operated manually by a physician. In another exemplary embodiment, the movement of the sheath 10 can be controlled and operated by an automated guidance system, such as, for example and without limitation, a robotic-based system or a magnetic-based system. In an exemplary embodiment where the sheath 10 is configured for physician control, the sheath 10 includes a steering mechanism 34. A detailed description of an exemplary steering mechanism, such as steering mechanism 34, is set forth in U.S. Patent Application Publication No. 2007/0299424 entitled "Steerable Catheter Using Flat Pull Wires and Method of Making Same," filed on Dec. 29, 2006, the disclosure of which is hereby incorporated by reference in its entirety. With reference to FIGS. 1 and 3, the steering mechanism 34 is briefly described. In an exemplary embodiment, the steering mechanism 34 comprises a handle 36, an anchoring structure 38 disposed in the shaft 12 of the sheath 10, and means 32 for deflecting the shaft 12.

Referring back to FIG. 1, the handle 36 is coupled to the shaft 12 at the proximal end 14 thereof. In an exemplary embodiment, the handle 36 provides a location for the physician/clinician to hold the sheath 10 and, in an exemplary embodiment, is operative to, among other things, effect movement (i.e., deflection) of the distal end 16 of the shaft 12 in one or more directions. The handle 36 is conventional in the art and it is understood that the construction of the handle 36 can vary.

In an exemplary embodiment, the handle 36 includes an actuator 40 disposed thereon or in close proximity thereto. The actuator 40 is configured to be selectively manipulated to cause the distal end 16 of the sheath 10 to deflect in one or more directions. More particularly, the manipulation of the actuator 40 causes the means 32 for deflecting the shaft 12 to be pushed or pulled (e.g., the length of the means 32 for deflecting the shaft 12 is increased or decreased), thereby effecting movement of the anchoring structure 38, and thus, the shaft 12. The actuator 40 can take a number of forms known in the art. For example, the actuator 40 can comprise a rotatable actuator, as illustrated in FIG. 1, that causes the sheath 10 (and the shaft thereof 12 in particular) to be deflected in one direction when rotated one way, and to deflect in another direction when rotated in the other way. Additionally, the actuator 40 can control the extent to which the shaft 12 is able to deflect. For instance, the actuator 40 can allow the shaft 12 to deflect to create a soft curve of the shaft (e.g., the distal end 16 of the shaft 12 deflects about 90° relative to the axis 20 of the shaft 12). Additionally, or in the alternative, the actuator 40 can allow the shaft 12 to deflect to create a more tight curve (e.g., the distal end 16 of the shaft 12 deflects about 180° relative to the axis 20 of the shaft 12). In an embodiment, the shaft 12 can be configured to deflect in a tight curve in one direction and to deflect in a more tight curve in another direction. It will be appreciated that while only a rotatable actuator is described in detail, the actuator 40 can take on any form known in the art that effects movement of the distal portion 16 of the sheath 10 or other medical device.

Referring now to FIG. 3, a depiction of a portion of the shaft 12 having the inner liner 22 surrounding the anchoring structure 38 cut away is illustrated. For example and without limitation, the anchoring structure 38 can comprise a ring (e.g., pull ring). The anchoring structure 38 is anchored to the shaft 12 at or near the distal end 16 thereof. One exemplary means by which the anchoring structure 38 is anchored is described in U.S. Patent Application Publication No. 2007/0199424 entitled "Steerable Catheter Using Flat Pull Wires and Method of Making Same" filed on Dec. 29, 2006, the entire disclosure of which was incorporated by reference above. Accordingly, as the means 32 for deflecting the shaft 12 are pulled and/or pushed, the means 12 push and pull the anchoring structure 38, thereby causing the shaft 12 to move (e.g., deflect). Accordingly, the physician manipulates the actuator 40 to cause the distal end 16 of the shaft 12 to move in a certain direction. The actuator 40 pulls and/or pushes the proper means 32 for deflecting the shaft (e.g., pull wires), which then causes the anchoring structure 38 (and therefore the shaft 12) to move as directed.

Means 32 for deflecting the shaft 12 are coupled at a first end to the actuator 40 and at a second opposing end to the anchoring structure 38. Means 32 for deflecting the shaft 12 can be extracted through the inner liner 22 for connection to the anchoring structure 38. Means 32 for deflecting the shaft 12 can comprise, for example and without limitation, steering or pull wires or other deflectable elements associated with a steering mechanism for the sheath 10. Means 32 for deflecting the shaft 12 can be coupled with both the handle 36 and the anchoring structure 38 and can be disposed within the shaft 12 of the sheath. In particular, at least a portion of means 32 for deflecting the shaft 12 are disposed within minor lumens (i.e., minor lumens $28_1$, $28_2$) in the inner liner 22 and are configured to extend from the handle 36 to the anchoring structure 38 (best shown in FIG. 3). In an exemplary embodiment, the means 32 for deflecting the shaft 12 have a rectangular cross-section. In other exemplary embodiments, the means 32 for deflecting the shaft 12 can have a cross-sectional shape other than rectangular, such as, for example and without limitation, a round or circular cross-sectional shape. Means 32 for deflecting the shaft 12 can comprise two pull wires that are disposed approximately 180° apart from each other around the circumference of the inner liner 22. The steering mechanism 34 can comprise a number of different pull wire arrangements. For example and without limitation, in other embodiments, the steering mechanism 34 can include four pull wires that are disposed approximately 90° apart from each other around the circumference of the inner liner 22.

Figure 4:
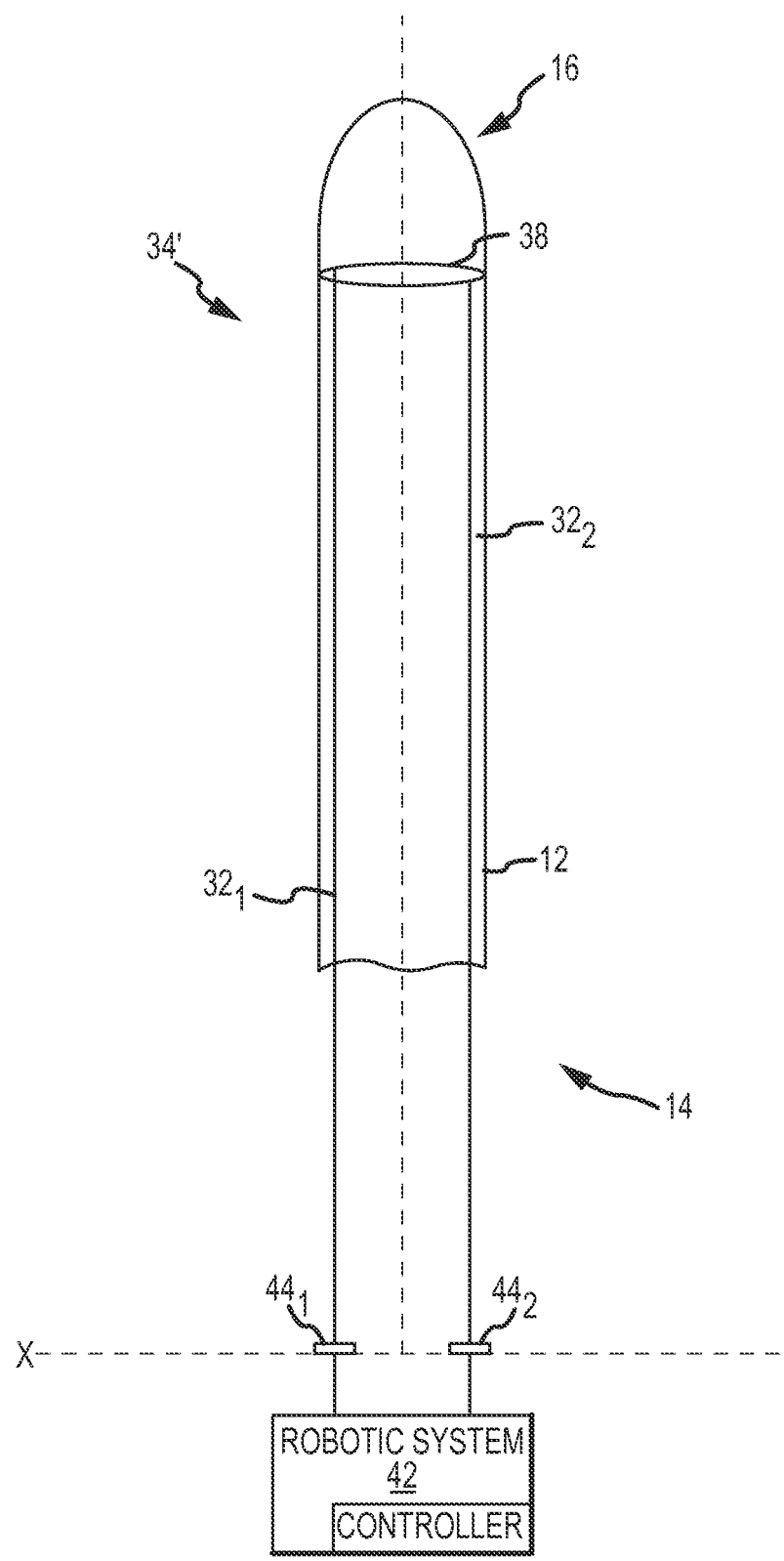
FIG. 4 is a diagrammatic and schematic view of another exemplary embodiment of the medical device illustrated in FIG. 1 showing the medical device used in connection with an exemplary embodiment of an automated guidance system.
Figure 5:
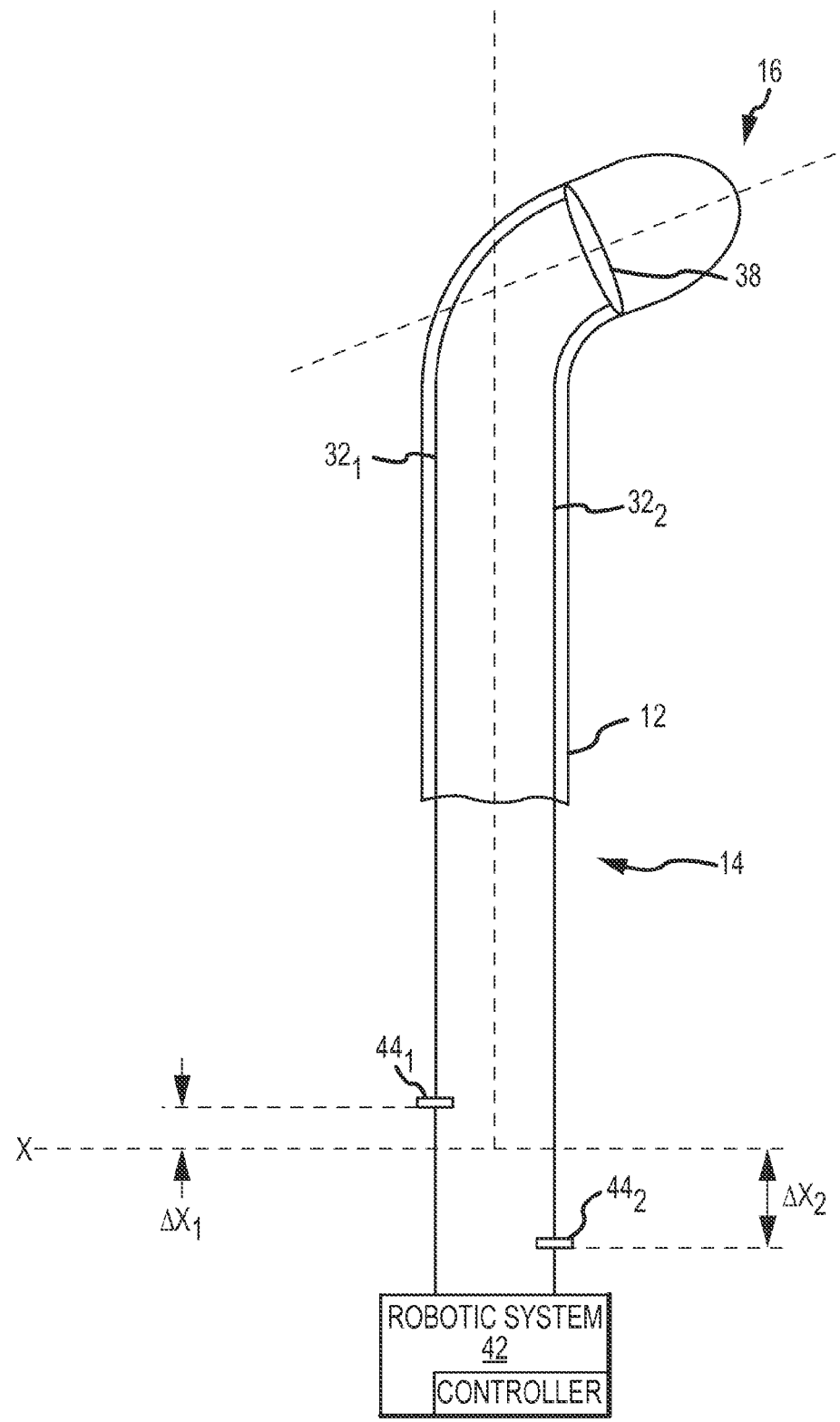
FIG. 5 is a diagrammatic and schematic view of another exemplary embodiment of the medical device illustrated in FIG. 4, wherein the distal end of the medical device is deflected.

In another exemplary embodiment, rather than being configured for manual control, the sheath 10 is controlled by an automatic guidance system 42. With reference to FIGS. 4-5, in one exemplary embodiment, the automated guidance system 42 is a robotic system (i.e., robotic system 42). In such an embodiment, the sheath 10 includes a steering mechanism 34' that is coupled with the robotic system 42 and acts in concert with and under the control of, the robotic system 42 to effect movement of the distal end 16 of the shaft 12. Detailed descriptions of exemplary arrangements/configurations by which a robotic system controls the movement of a medical device are set forth in PCT Patent Application No. PCT/2009/038597 entitled "Robotic Catheter System with Dynamic Response," filed on Mar. 27, 2009 (International Publication No. WO/2009/120982), and U.S. Patent Application Publication No. 2009/0247993 entitled "Robotic Catheter System," filed on Dec. 31, 2008, the disclosures of which are hereby incorporated by reference in their entireties. In an exemplary embodiment, the steering mechanism 34' comprises one or more pull wires 32 (i.e., $32_1$ and $32_2$ in FIGS. 4-5) and an anchoring structure 38. The description above with respect to these components applies here with equal force, and therefore, will not be repeated. However, unlike the embodiment described above, the steering mechanism 34' further comprises one or more control members 44 (i.e., $44_1$ and $44_2$ in FIGS. 4-5) equal to the number of pull wires 32, and each control member 44 is affixed or coupled to a respective pull wire 32. The control member 44 are configured to interface or operatively connect control devices, such as, for example, motors or associated linkage or intermediate components thereof, to the pull wires 32. In such an embodiment, the control devices are controlled by a controller, which, in turn, can be fully automated and/or responsive to user inputs relating to the driving or steering of the sheath 10.

In either instance, movement of the control devices (e.g., movement of a motor shaft) is translated to cause one or more of the control members 44 to move, thereby resulting in the desired movement of the sheath 10, and the shaft 12 thereof in particular. For example, FIG. 4 illustrates the shaft 12 in an undeflected state. Thus, both of the control members $44_1$, $44_2$ are co-located at position X. However, FIG. 5 illustrates the shaft 12 in a deflected state. In this instance, the control member $44_1$ has been pushed toward the distal end 16 of the shaft 12 a distance of ΔX1, while the control member $44_2$ has been pulled away from the distal end 16 of the shaft 12 a distance of ΔX2. Accordingly, the robotic system 42 is configured to manipulate the positions of the control members 44 of the steering mechanism 34' to effect movement of the shaft 12, and the distal end 16 thereof, in particular.

While the description of an automated sheath control system 42 has been with respect to one particular robotic system, other automated guidance systems and other types of robotic systems can be used. Accordingly, automated guidance systems other than robotic systems, and robotic-based automatic guidance systems other than that described with particularity above, remain within the spirit and scope of the present disclosure. Referring back to FIG. 1, the sheath 10 can further include an integrated hemostasis valve 45. The hemostasis valve 45 can provide effective hemostasis and can seal down to a 0.014 inch (0.356 mm) guidewire.

Figure 6:
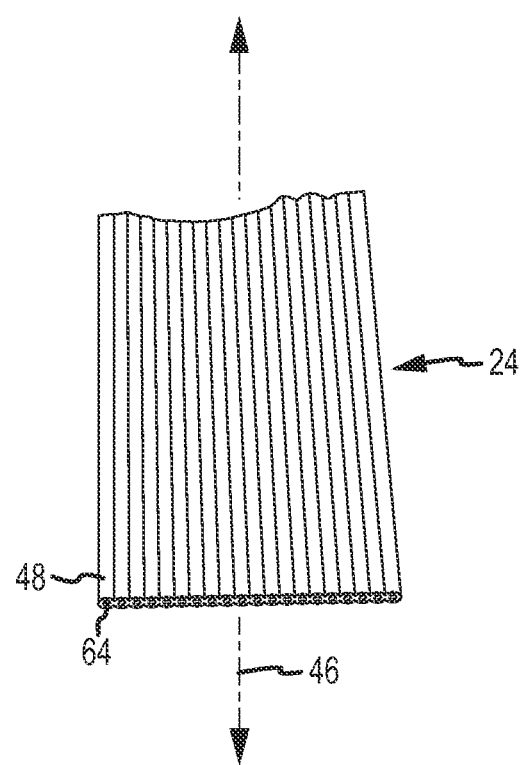
FIG. 6 is a perspective view of a generally planar element of the medical device of FIG. 1.
Figure 7A:
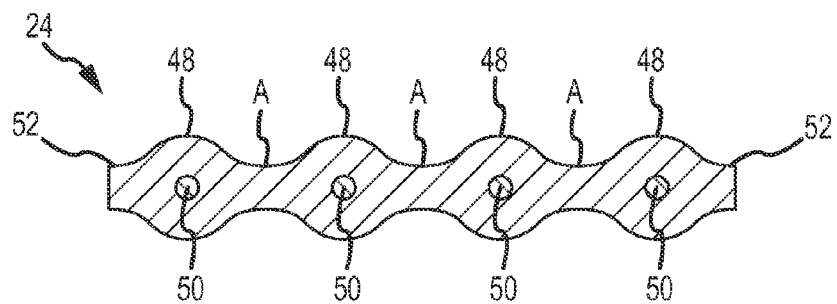
FIGS. 7A-7B are cross-sectional views of the generally planar element of FIG. 6 in accordance with various embodiments of the disclosure.
Figure 7B:
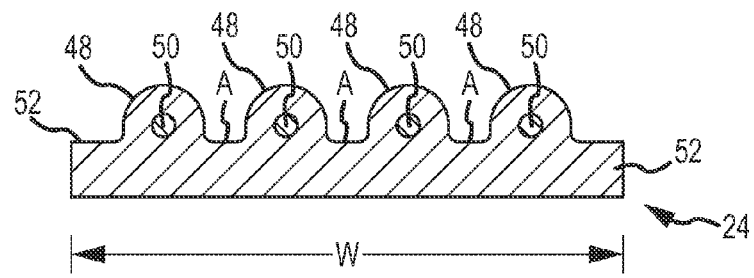
Figure 8:
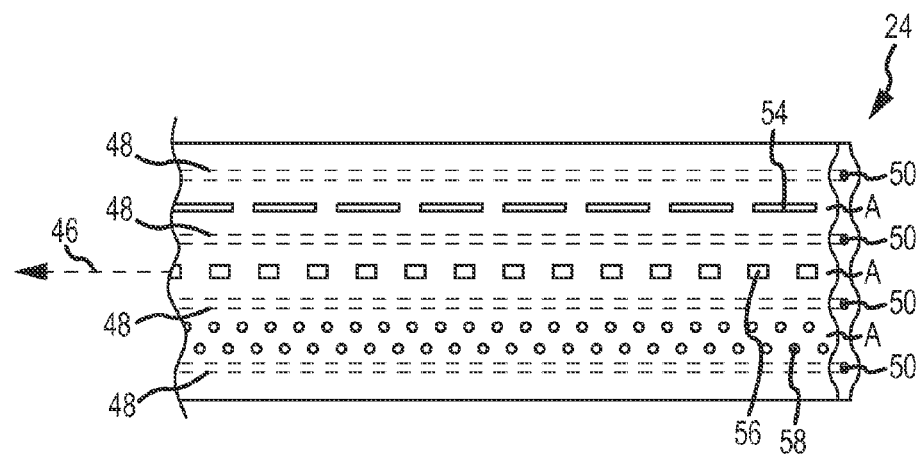
FIG. 8 is a schematic view of the generally planar element of FIG. 6 showing the various patterns of material removal from the generally planar element in accordance with various embodiments of the disclosure.

The shaft 12 further comprises a generally planar element 24 wrapped in a spiral pattern on the inner liner 22. Referring now to FIGS. 6-8, the generally planar element 24 has a longitudinal axis 46 and a plurality of longitudinally extending ribs 48. Each of the plurality of ribs 48 extends along the longitudinal axis 46. In an embodiment as generally illustrated in FIG. 6, the generally planar element 24 can comprise a ribbon wire with built-in electrical conductors or wires 64 as described in more detail below disposed in the longitudinally extending ribs 48. A generally planar element 24 comprising ribbon wire enables the shaft 12 to have desirable torque and stiffness. Depending upon whether the electrical conductors or wires 64 are needed in a particular design, the wires 64 can be left in place within the longitudinally extending ribs 48 if no electrode connections are needed, or the wires 64 can be extracted at both ends to create electrode connections. In an embodiment as generally illustrated in FIGS. 7A-7B and 8, each of the plurality of ribs 48 has a corresponding lumen 50 disposed therein. An inner diameter of each of the corresponding lumens 50 can be about 0.010 inches (0.254 mm) in an exemplary embodiment.

The width W of the generally planar element can be about 0.5 to 1.0 inches (12.7 to 25.4 mm) in an exemplary embodiment. If the width W is more narrow, the generally planar element 24 will be more stiff. If the width W is more wide, the generally planar element 24 will be less stiff. The generally planar element 24 can include approximately ten to twelve longitudinally extending ribs 48 in accordance with some embodiments of the disclosure. However, the generally planar element 24 can include fewer or more longitudinally extending ribs 48 in accordance with various embodiments of the disclosure. The number of longitudinally extending ribs 48 can depend on the desired characteristics of the sheath 10. Each of the longitudinally extending ribs 48 can be substantially equally spaced along the width W of the generally planar element 24 and can include a flat portion 52 on opposing sides of the generally planar element. If the longitudinally extending ribs 48 are placed more closely together along the width W of the generally planar element 24, then the generally planar element 24 will be more stiff. If the longitudinally extending ribs 48 are placed further apart along the width W of the generally planar element 24, then the generally planar element 24 will be less stiff. The generally planar element 24 is relatively thin. For example, in one embodiment, the generally planar element 24 has a thickness on the order of about 0.002 to 0.050 inches (0.0508 to 1.27 mm). The length of the generally planar element 24 can vary in accordance with the desired length of the sheath 10. However, it is noted that the same generally planar element 24 can be wrapped in a spiral pattern about sheaths 10 of various sizes. Although exemplary dimensions are set forth in detail, the various dimensions for the generally planar element 24 can vary in accordance with different embodiments of the disclosure. In accordance with one exemplary embodiment generally illustrated in FIG. 7A, the longitudinally extending ribs 48 can be substantially spherical in cross-section. In accordance with another exemplary embodiment generally illustrated in FIG. 7B, the longitudinally extending ribs 48 can be substantially hemispherical in cross-section, which can allow for a flat surface on the generally planar element that opposes the longitudinally extending ribs 48. In general, it can be desirable to have a configuration that allows for a thinner and/or slimmer design for the generally planar element 24.

The generally planar element 24 can comprise a polymeric material. For example and without limitation, the polymeric material of the generally planar element can comprise PEEK in accordance with an embodiment of the disclosure. PEEK can be especially well-suited for the disclosure because of its durable mechanical properties, excellent abrasion resistance, chemical and biological inertness, and its ability to withstand high temperatures and be processed into tapes and/or tubing. It will be appreciated by those having ordinary skill in the art that the generally planar element can be formed of a polymeric material other than PEEK. For example, in other exemplary embodiments, the generally planar element 24 is comprised of polymeric materials, such as, for example and without limitation, nylon, PTFE, or combinations thereof. Accordingly, sheaths having a generally planar element 24 made of materials other than PEEK remain within the spirit and scope of the disclosure. The generally planar element 24 can be available for purchase directly from a manufacturer and can be extruded in different patterns in order to achieve the same mechanical properties as a braided wire assembly in accordance with embodiments of the disclosure.

As best seen in FIG. 8, at least a portion of the generally planar element 24 can be selectively removed in accordance with an embodiment of the disclosure. For example and without limitation, at least a portion of the generally planar element 24 can be selectively removed by due cutting or laser cutting or a combination thereof. The selective removal of at least a portion of the generally planar element 24 is configured to create a mesh-like area of the generally planar element 24 through which the outer layer 26 can bond with the inner liner 22 during manufacturing of the sheath 10. In particular, the polymeric material of the outer layer 26 melts and flows into the mesh-like areas of the generally planar element 24 and bonds to the inner liner 22 during a reflow process performed on the shaft 12. The portion of the generally planar element 24 that can be selectively removed is located in an area A between adjacent ribs 48. FIG. 8 is a schematic view of the various patterns of material removal from the generally planar element 24 in accordance with various embodiments of the disclosure. For example, in a first embodiment, material can be selectively removed from the generally planar element 24 in a pattern of one or more rows of rectangular shaped apertures 54 extending along the longitudinal axis 46 of the generally planar element 24. In a second embodiment, material can be selectively removed from the generally planar element 24 in a pattern of one or more rows of square shaped apertures 56 extending along the longitudinal axis 46 of the generally planar element 24. In a third embodiment, material can be selectively removed from the generally planar element 24 in a pattern of one or more rows of round apertures 58 extending along the longitudinal axis 46 of the generally planar element 24. Although these particular patterns of material removal were mentioned in detail, the patterns of material removal can vary in accordance with different embodiments of the disclosure and can be selected and/or adjusted to prevent delamination of the outer layer 26. In some embodiments, the selective removal of at least a portion of the generally planar element 24 can be unnecessary if the generally planar element 24 can be manufactured in a configuration that is more compatible with construction of the sheath 10 and can allow bonding of the inner liner 22 and the outer layer 26.

The generally planar element 24 is wrapped in a spiral or helical pattern about the outer surface 29 of the inner liner 22 on the mandrel. The generally planar element 24 is tacked down and/or adhered to the outer surface 29 of the inner liner 22 in an embodiment of the disclosure. For example and without limitation, the generally planar element 24 can be wrapped in a spiral or helical pattern by starting at a first end of the shaft 12 and can be tacked down at the first end with a first heat shrink tube that surrounds and/or encircles at least a portion of the generally planar element 24 at a first end of the shaft 12. The first heat shrink tube can extend only a relatively small distance along the length of the shaft 12 at the first end of the shaft 12 in an embodiment of the disclosure. The generally planar element 24 is then wrapped in a spiral or helical pattern and/or coiled along the length of the shaft 12. The generally planar element 24 can be wrapped in a spiral or helical pattern and/or coiled along the entire length (e.g., from the proximal end 14 to the distal end 16) of the shaft 12 or can extend only along one or more portions of the length of the shaft 12 in some embodiments. The generally planar element 24 can be tacked down at the second end of the shaft 12 (or any second location along the shaft 12) with a second heat shrink tube that surrounds and/or encircles at least a portion of the generally planar element 24 at a second end of the shaft 12 (or any second location along the shaft 12). The second heat shrink tube can extend only a relatively small distance along the length of the shaft 12 at the second end of the shaft 12 (or the second location along the shaft 12) in an embodiment of the disclosure. The first and second heat shrink tubes can comprise any number of different materials. In an exemplary embodiment, the first and second heat shrink tubes can comprise a fluoropolymer (e.g., fluorinated ethylene polypropylene (FEP)) or polyolefin. The first and second heat shrink tubes are sized to fit over the generally planar element 24 of the shaft 12. During manufacture, the shaft 12 (including the first and second heat shrink tubes and the generally planar element 24) can be subjected to a heat treating process, such as, for example and without limitation, a preliminary reflow process. During this preliminary reflow process, the first and second heat shrink tubes shrink when exposed to a suitable amount of heat, thereby holding the generally planar element 24 in place on the shaft 12. Other processes known to those of ordinary skill in the art can be used for adhering and/or tacking down the generally planar element 24.

As described in more detail below, the generally planar element 24 can have substantially equal spaces between adjacent turns of the generally planar element 24 as it is wrapped about the outer surface 29 of the inner liner 22. In other words, the pitch of the spiral can be substantially equal along the length of the sheath 10. The spacing between adjacent turns (i.e., pitch) is adjustable depending at least in part on the desired flexibility of the sheath 10 and/or the number of electrical conductors or wires 64 as described in more detail below. The spacing between adjacent turns (i.e., pitch) is also adjustable based on the spacing of the longitudinally extending ribs 48 along the width W of the generally planar element 24 and desired performance of the shaft 12. The generally planar element 24 can extend the entire length of the shaft 12 (i.e., from the proximal end 14 to the distal end 16) or less than the entire length of the shaft 12. The generally planar element 24 can shrink to the mandrel during processing such that there will be no spaces between adjacent turns of the generally planar element 24 after processing. The generally planar element 24 can be wrapped tightly to the outer diameter of the mandrel in order to reduce the overall diameter of the sheath 10. It is known by those of ordinary skill in the art to measure tension of the generally planar element 24 in accordance with fixtures and/or tools that are conventional in the art. Therefore, with proper fixtures and tools, it is possible to wind the generally planar element 24 around the sheath 10 with a constant tension. There are many advantages to the use of a generally planar element 24 wrapped around in a spiral pattern about the outer surface 29 of the inner liner 22. For example and without limitation, the generally planar element 24 provides another layer of protection to the inner liner 22 during further processing while avoiding potential damage to the inner liner 22. In contrast, braided wire assemblies made of metal can have sharp edges that can potentially damage the delicate inner liner 22, thereby causing leak and loss of deflection of the sheath 10. Braided wire assemblies also require significant processing during manufacturing, which makes the manufacturing process more timely and complex. In particular, braided wire assemblies are manually stretched over the inner liner, and it is difficult to maintain a uniform tension on braided wire assemblies during stretching. It can be difficult to know how taut the braid is being pulled, since the braid can move in unpredictable patterns, which can create areas of high tensions, can cause flaring, and can distort the direction of the pull wires. In addition, braided wire assemblies require annealing (i.e., to prevent the braided wire assembly from flaring during production, thereby exposing the braid on the surface of the sheath), cutting, and constant preening during manufacturing to prevent scrap. Moreover, the wire is braided into several different patterns and over several different mandrels for different deflection patterns for different curl sizes and diameters.

Figure 9:
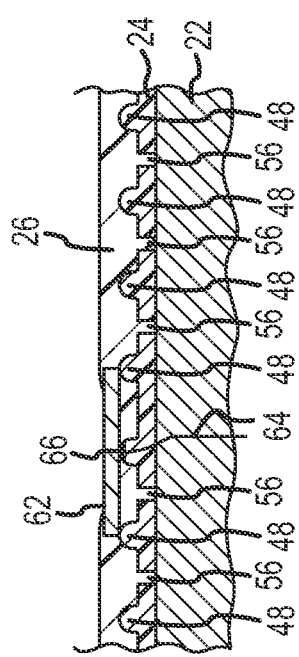
FIG. 9 is a schematic partial side sectional view of a portion of the medical device of FIG. 1 with an electrode mounted thereon.

Referring back to FIG. 2, at least a portion of the outer layer 26 is disposed adjacent to the generally planar element 24. At least a portion of the outer layer 26 can also be disposed adjacent to the inner liner 22, and in particular, the portions of the outer layer 26 that can be disposed adjacent to the inner liner 22 can correspond to those areas A where portions of the generally planar element 24 have been removed to create a mesh-like area in the generally planar element 24 through which the outer layer 26 can bond with the inner liner 22. The outer layer 26 melts and flows into the mesh-like areas of the generally planar element 24 and bonds to the inner liner 22 during the reflow process performed on the shaft. The outer layer 26 also fills in the gaps between the longitudinally extending ribs 48, the gaps generally designated as areas A in FIGS. 7A-7B and 8. Accordingly, the outer layer 26 can prevent the generally planar element 24 wrapped in a spiral pattern on the outer surface 29 of the inner liner 22 from collapsing, compressing, and/or expanding during manipulation of the sheath 10 when the sheath 10 is in compression, tension, and/or torque. In this way, a sheath 10 in accordance with the instant disclosure can have the same functionality of current sheaths without requiring a metal braided wire assembly. Referring now to FIG. 9, the outer layer 26 is shown melted in areas A between adjacent longitudinally extending ribs 48 and, further, under an electrode 62 to be described in more detail below. As mentioned above, in some embodiments, at least a portion of the polymeric material comprising the outer layer 26 can flow through the generally planar element 24 (even if a portion of the generally planar element 24 has not been selectively removed) because the configuration of the generally planar element 24 can be more compatible with construction of the sheath 10. At least a portion of the polymeric material comprising the outer layer 26 can bond with at least a portion of the inner liner 22.

The outer layer 26 comprises a polymeric material in accordance with an embodiment of the disclosure. The outer layer 26 can be formed of a single polymeric material, or alternatively, a combination of different components/materials (e.g., various tubing) that, after the application of a reflow process on at least a portion of the shaft 12, combine to form the outer layer 26. In the exemplary embodiment illustrated in FIG. 2, the outer layer 26 comprises one or more layers of polymeric material that are placed over the inner liner 22. The polymeric material can be in the form of one or more extruded polymer tube(s). The polymer tube(s) making up the outer layer 26 can comprise one or more of any number of polymeric materials, such as, for example and without limitation, polyether block amides (e.g., polyether block amides sold under the trademark PEBAX® and generally available from Arkema France), polyamides (e.g., nylon), PTFE, etched PTFE, other thermoplastic elastomers, or combinations thereof. In a particular embodiment, the outer layer 26 can comprise a first polymer tube of nylon located on the proximal end 14 of shaft 12 and a second polymer tube of polyether block amide sold under the trademark PEBAX® on the distal end 16 of shaft 12. The distal end 16 of shaft 12 can comprise a soft, atraumatic tip. The polymer tube(s) making up the outer layer 26 can be formed of a single piece of tubing or multiple pieces of tubing. Whether formed of a single piece or multiple pieces, the tube(s) can have a uniform hardness or durometer throughout. Alternatively, different portions of the tube(s) can have different durometers (e.g., the shaft 12 can have a variable durometer from the proximal end 14 to the distal end 16). In an embodiment, where the tube(s) is formed of multiple pieces, the pieces can be affixed together end to end, or portions of adjacent pieces can overlap each other. These pieces can be coupled or bonded together to form the shaft 12 during a reflow process performed thereon.

In addition to the above, in an exemplary embodiment, the shaft 12 of the sheath 10 can further include a layer 60 of heat shrink material on the outer surface thereof. With reference to FIG. 2, the heat shrink layer 60 is disposed adjacent to the polymeric material of the outer layer 26 (e.g., the polymer tube(s)) such that the outer layer 26 is disposed between the inner liner 22 and the heat shrink layer 60. The heat shrink layer 60 can be formed of a number of different types of heat shrink materials. In an exemplary embodiment, the heat shrink layer 60 comprises a fluoropolymer or polyolefin material, and more particularly, a tube formed of such a material sized to fit over the outer layer 26 of the shaft 12. One example of a suitable material for the heat shrink layer 60 is FEP. As will be described in greater detail below, one purpose of the heat shrink material layer 60 relates to the manufacturing process of the sheath 10. More particularly, during manufacture, the shaft 12 is subjected to a heat treating process, such as, for example and without limitation, a reflow process. During this process, the heat shrink layer 60 is caused to shrink when exposed to a suitable amount of heat. The heat applied to the shaft 12 also causes the polymeric material of the polymer tube(s) of the outer layer 26 to melt, and the shrinking of the heat shrink layer 60 forces the polymeric material to flow into contact with generally planar element 24 and the inner liner 22. In an exemplary embodiment, the heat shrink layer material 60 remains as the outermost layer of the shaft 12. However, in another exemplary embodiment, the heat shrink material layer 60 is removed following the reflow process, and therefore, the polymer tube(s) comprising the outer layer 26 is the outermost layer of the shaft 12. Accordingly, sheaths 10 that when fully assembled have a heat shrink material layer 60 and sheaths that when fully assembled do not have a heat shrink material layer 60, both remain within the spirit and scope of the present disclosure.

In an exemplary embodiment, the shaft 12 can further include a lubricious coating (not shown) that can cover all or a portion of the shaft 12. In an exemplary embodiment, the coating comprises siloxane. However, in other exemplary embodiments, the coating can comprise any of a number of suitable hydrophilic coatings, such as for example, polymeric material with lubricious qualities such as those sold under the trademark HYDROMER® and generally available from Hydromer, Inc. or under the trademark HYDAK® and generally available from Biocoat, Incorporated. The purpose of the lubricious coating, which can be adjacent to either the polymer tube(s) of the outer layer 26 or the heat shrink layer 60 (if the shaft has a heat shrink layer 60), is to provide the shaft 12 with a smooth and slippery surface that is free of sharp edges, such that the shaft 12 can move with ease when inserted into an anatomical structure.

Figure 10:
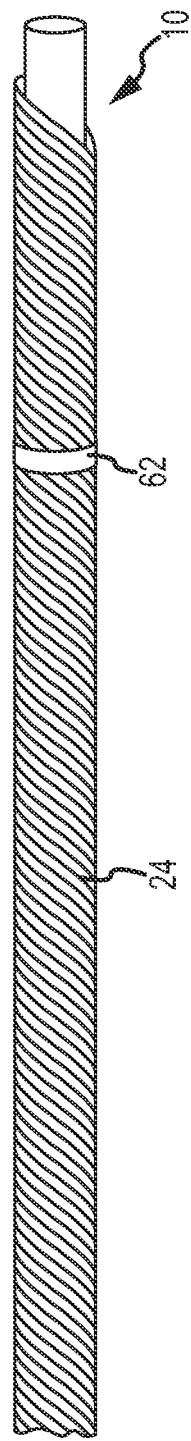
FIG. 10 is a side view of a portion of the medical device of FIG. 1 with an electrode mounted thereon.

With reference to FIG. 10, the sheath 10 can comprise one or more electrodes 62 mounted thereon. As illustrated in FIG. 10, and as will be described in greater detail below, the electrode(s) 62 are mounted on the shaft 12 at the distal end 16 thereof. However, in other exemplary embodiments, one or more of the electrodes 62 can be mounted at locations on the shaft 12 that are more proximal than the distal end 16. The electrode(s) 62 can be mounted on deflectable portions of the shaft 12 and/or non-deflectable portions of the shaft 12. The electrodes(s) 62 can have a number of spacing configurations. The electrode(s) 62 can comprise any number of types of electrodes and can be used for any number of purposes. For example, the electrodes 62 can comprise one or more of magnetic coils, ring electrodes, tip electrodes, or a combination thereof. Further, the electrodes 62 can be used for a number of different purposes or to perform a number of different functions. For example, the electrodes 62 can be used in the pacing of the heart, monitoring electrocardiograph (ECG) signals, detecting location/position of the electrode 62 (and therefore the sheath 10), mapping, navigation, and/or visualization of the sheath 10, and the like. Additionally, one or more of the electrodes 62 can be formed of a radio-opaque material, such as, for example and without limitation, a metallic material, such as, for example, platinum or another dense material. This permits the visualization of the electrodes 62 by an x-ray based visualization system, such as, for example, a fluoroscopic system. Further, the electrodes 62 can be low impedance electrodes (e.g., $\leq 600\Omega$).

Each electrode 62 has one or more elongate electrical conductors or wires 64 associated therewith and electrically coupled thereto. FIG. 11 is a side view of a sheath 10 with a plurality of electrical conductors or wires 64 exposed. The corresponding lumen 50 of each of the plurality of ribs 48 of the generally planar element 24 is configured to house, for example, the electrical conductors or wires 64 associated with the electrodes 62. FIG. 12 is a schematic partial side view of a portion of sheath 10 with an electrode 62 mounted thereon. As generally illustrated in FIG. 12, in an exemplary embodiment, each corresponding lumen 50 is configured to house the electrical conductor or wire 64 of single corresponding electrode 62. Accordingly, the lumens 50 of the longitudinally extending ribs 48 isolate the electrical wires 64 from each other. In other embodiments as generally illustrated in FIG. 6, each longitudinally extending rib 48 of the generally planar element 24 can house the electrical conductor or wire 64 of a single corresponding electrode (e.g., in the wall of one or more of the longitudinally extending ribs 48 of the ribbon wire). The number of electrical conductors or wires 64 can affect the number of longitudinally extending ribs 48 that are needed. In some embodiments, not every lumen 50 of the longitudinally extending ribs 48 (or the walls of the longitudinally extending ribs 48 in other embodiments) can house an electrical conductor or wire 64. The number of electrical conductors or wires 64 can also affect the required spacing between adjacent turns of the generally planar element 24 as it is wound in a spiral pattern. The number and spacing between electrical conductors or wires 64 can be modified and/or adjusted depending at least in part on the desired performance of the shaft 12. Still referring to FIG. 12, a small aperture 66 is made on an outer radial surface of rib 48 through which the electrical conductor or wire 64 can be threaded. The electrical conductors or wires 64 can be extracted to an area distal of the area of extraction for the means 32 for deflecting the shaft 12. The electrical conductors or wires 64 can include a thin coating of insulation in accordance with an embodiment of the disclosure to prevent shorting where the electrical conductors or wires 64 exit the generally planar element 24. Accordingly, the electrical conductor or wire 64 of a single electrode 62 is electrically connected to the electrode 62, passes through the small aperture 66 made on a surface of rib 48 of the generally planar element 24, and is disposed within the longitudinally extending rib and/or the lumen 50 of the longitudinally extending rib 48 of the generally planar element 24. When disposed within the longitudinally extending ribs 48 or the lumens 50, the electrical conductors or wires 64 are permitted to move within the longitudinally extending rib 48 or the lumen 50 of the longitudinally extending rib 48 as the shaft 12 is deflected. The lumen 50 of the longitudinally extending rib 48 extends at least from a location on the shaft 12 near where the electrode 62 is mounted to the proximal end 14 of the shaft 12 such that the electrical conductor or wire 64 can be coupled to an interconnect or table connector (not shown), which allows the electrode 62 to be coupled with other devices, such a computer, a system for visualization, mapping, and/or navigation, and the like. The interconnect is conventional in the art and is disposed at the proximal end 14 of the shaft 12.

In those embodiments of the instant disclosure that include electrodes 62, the reflow process can be applied on at least a portion of the shaft 12 to form the outer layer 26 after the electrodes 62 are mounted onto the shaft 12. Once the electrodes 62 are in place, the outer layer 26 can be reflowed as described herein.

Each electrode 62 can be slip fit directly over the generally planar element 24 that has been wrapped in a spiral pattern on the outer surface 29 of the inner liner 22 of the sheath because the generally planar element 24 comprises a polymeric material that is not electrically conductive. The ability to directly place each electrode 62 over the generally planar element 24 is another advantage of the generally planar element 24 over braided wire assemblies. If a sheath includes a braided wire assembly, electrodes must be placed over the outer layer of a sheath, rather than the braided wire assembly, in order to avoid shorting the electrodes. This requires a larger diameter electrode to fit over both a braided wire assembly and a thin layer of material forming the outer layer of the sheath. This also requires puncturing a hole through the outer layer through which the electrical conductors or wires of the electrode need to extend. This also requires additional processing steps to eventually cover the electrodes with a polymeric material. In contrast, the direct placement of each electrode 62 over the generally planar element 24 of the sheath 10 in connection with the instant disclosure allows for a smaller diameter electrode 62 (thereby making a smaller outer diameter profile for sheath 10 possible) and removes the need to puncture a hole through the outer layer and/or utilize additional processing steps to cover the electrodes with a polymeric material.

It will be appreciated that in addition to the structure of the sheath 10 described above, another aspect of the present disclosure is a method of manufacturing a medical device, such as, for example, the sheath 10. As was noted above, the following description will be limited to an embodiment wherein the medical device is a sheath 10. It will be appreciated, however, that the methodology can be applied to medical devices other than a sheath and that those medical devices remain within the spirit and scope of the present disclosure.

Figure 13:
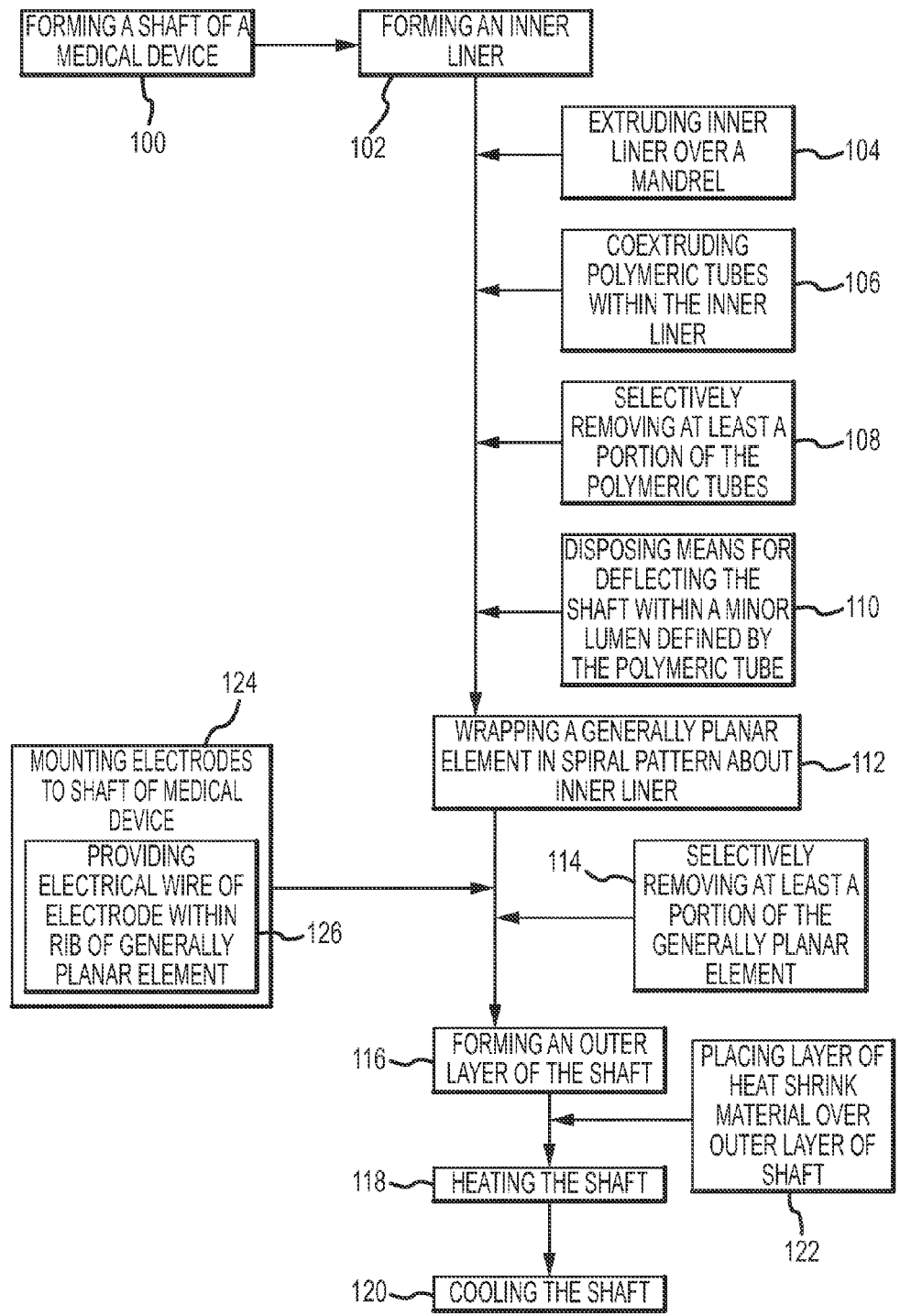
FIG. 13 is a flow diagram illustrating an exemplary embodiment of a method of manufacturing a medical device in accordance with the present teachings.
Figure 14:
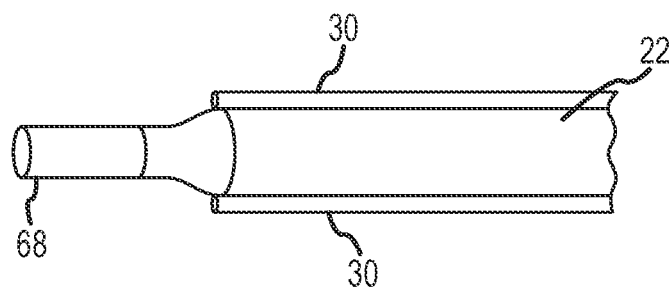
FIG. 14 is a schematic view of a mandrel used in accordance with an exemplary embodiment of a method of manufacturing a medical device in accordance with the present teachings.

With reference to FIG. 13, in an exemplary embodiment, the method comprises a step 100 of forming a shaft 12 of the sheath 10. The forming a shaft step 100 can comprise a number of substeps. In an exemplary embodiment, a substep 102 comprises forming an inner liner, such as for example, the inner liner 22 described above. The inner liner 22 has a tubular shape, and has an inner surface 28 and an outer surface 29. In an exemplary embodiment, the inner liner is formed by extruding the inner liner 22 over a mandrel (step 104). In this embodiment, the mandrel is removed at or near the end of the manufacturing process, thereby resulting in the creation of the major lumen 18 in the inner liner 22. Referring now to FIG. 14, an exemplary tapered mandrel 68 is generally illustrated.

The inner liner 22 is also formed by coextruding a plurality of polymeric tubes, such as for example, the polymeric tubes 30, within the inner liner 22 (step 106). Each tube 30 defines a minor lumen 32 therein in which, as was described above, houses a means 32 for deflecting shaft 12. A substep 108 comprises selectively removing at least a portion of each of the polymeric tubes 30. For example and without limitation, a lasering process can be used to selectively remove a contiguous portion of the polymeric tube 30 that is disposed at the distal end 16 of the shaft 12. The method can further comprise a step of inserting set-up wires into one or more of the minor lumens $28_1$, $28_2$ defined by the tubes 30. The purpose of set-up wires can be to prevent the tubes 30 from collapsing during the subsequent steps of the manufacturing process. Following the performance of one or more heat treating processes on the shaft 12 described hereinbelow, the set-up wires can be removed from the minor lumens $28_1$, $28_2$ and replaced with means 32 for deflecting the shaft 12 in at least one direction relative to a longitudinal axis 20 of the shaft 12. A substep 110 comprises disposing the means 32 for deflecting the shaft 12 within the minor lumens $28_1$, $28_2$ defined by the polymeric tubes 30. The inner liner comprises the first layer of the shaft 12 of the sheath 10.

Figure 15:
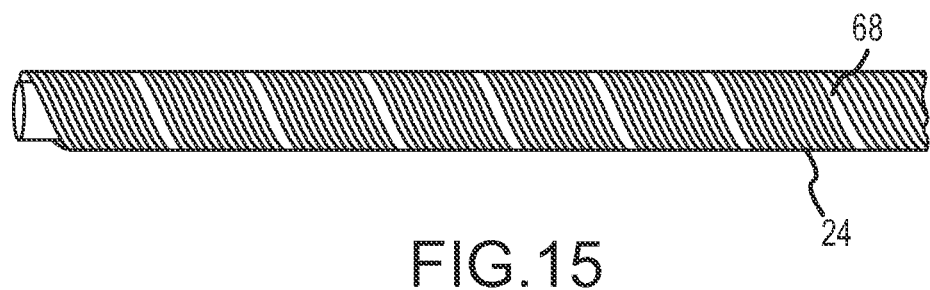
FIG. 15 is a schematic view of the spiral pattern of the generally planar element in accordance with an exemplary embodiment of a method of manufacturing a medical device in accordance with the present teachings.

The forming step 100 further comprises the substep 112 of wrapping a generally planar element comprising a polymeric material, such as for example the generally planar element 24 described above, in a spiral pattern about the outer tubular surface 29 of the inner liner 22. FIG. 15 generally illustrates the spiral pattern. As illustrated, there can be spaces between adjacent turns of the generally planar element 24 as it is wrapped about the outer surface 29 of the inner liner 22. The spacing between adjacent turns is adjustable depending at least in part on the desired flexibility of the sheath 10. The generally planar element 24 can be wrapped tightly to the outer diameter of the mandrel 68 in order to reduce the overall diameter of the sheath 10. The generally planar element 24 has a longitudinal axis 46 and a plurality of longitudinally extending ribs 48. In some embodiments, the generally planar element 24 comprises a ribbon wire having a plurality of longitudinally extending ribs 48 (e.g., with built-in electrical conductors or wires 64 that can or can not be used). In other embodiments, the generally planar element has a plurality of longitudinally extending ribs 48 each having a corresponding lumen 50 disposed therein. In an embodiment, a substep 114 comprises selectively removing at least a portion of the generally planar element 24. For example and without limitation, a laser cutting or die-cutting process can be used to remove at least a portion of the generally planar element 24 in an area between adjacent ribs 48. In other embodiments, it can be unnecessary to selectively remove at least a portion of the generally planar element 24 prior to forming an outer layer 26 of the shaft 12. In such embodiments, the generally planar element 24 can be manufactured in accordance with a configuration that is more compatible with construction of the sheath 10.

The forming step 100 further comprises a substep 116 of forming an outer layer 26 of the shaft 12, such as for example, the outer layer 26 described above. In an exemplary embodiment, substep 116 comprises covering the inner liner 22 and the generally planar element 24 with one or more layers of polymeric material to form the outer layer 26 by placing one or more tubes formed of a polymeric material over the inner liner 22 and the generally planar element 24. In an exemplary embodiment, the method further comprises performing one or more heat treating processes, such as, for example, a reflow process on at least a portion of the shaft 12, and the outer layer 26 thereof, in particular. Accordingly, in one such embodiment, the method comprises a step 118 of heating the shaft 12 to a temperature at which the polymeric material thereof melts and redistributes around the circumference of the shaft 12. In one exemplary embodiment, the temperature applied to the shaft 12 is 400 degrees (F.), and the rate of exposure is 1 cm/minute. It will be appreciated, however, that the temperature and the rate of exposure can vary depending on various factors, such as for example, the material used. Accordingly, the present disclosure is not meant to be limited to the specific temperatures and rate set forth above, and other temperatures and rates remain within the spirit and scope of the present disclosure. At least portion of the polymeric material compromising the outer layer 26 flows through the generally planar element 24 at an area A where at least a portion of the generally planar element 24 has been selectively removed (e.g., an area between adjacent ribs 48 of the generally planar element 24. Accordingly, at least a portion of the outer layer 26 is bonded to at least a portion of the inner liner 22. In other embodiments, at least a portion of the polymeric material comprising the outer layer 26 can flow through the generally planar element 24 (even without the step of selectively removing at least a portion of the generally planar element 24), thereby allowing at least a portion of the polymeric material comprising the outer layer 26 to bond to at least a portion of the inner liner 22.

Once the heating step 118 is complete, a step 120 of cooling the shaft 12, and therefore, the polymeric material is performed. In an exemplary embodiment, the cooling step 120 comprises letting the shaft 12 air-cool. However, in another exemplary embodiment, a cooling process can be performed on the shaft 12.

In an exemplary embodiment and prior to performing the heating step 118, the method further comprises a step 122 of placing a layer of heat shrink material, such as for example, the heat shrink material layer 60 described above, over the outer layer 26 of the shaft 12. The heat shrink material layer 60 is formed of a material that has a higher melt temperature than that of the polymeric material of the outer layer 26 such that when the heating step 118 is performed, the heat shrink material layer 60 retains its tubular shape and forces the polymeric material into the generally planar element 24 and into contact with the inner liner 22, but does not itself melt. In an exemplary embodiment, following the heating step 118 and either during or following the cool step 120, the heat shrink material layer 60 is removed. Alternatively, the heat shrink material layer 60 is not removed, but rather remains as part of the shaft 12. In an exemplary embodiment, following the cooling step 120, the method can further comprise a step of coating the outer surface of the shaft 12, with a lubricious coating.

In an exemplary embodiment, the method further comprises a step 124 of mounting one or more electrodes onto the shaft 12, such as electrodes 62. It can be desirable that the sheath 10, and the shaft 12 thereof in particular, be smooth and free of sharp edges. Accordingly, the mounting step 124 can comprise recessing the electrodes 62 into the outer layer 26. In an exemplary embodiment, this is done by swaging the outer surface of the electrodes 62 down, thereby forcing the bottom or inner surface of the electrodes 62 down and locking the electrodes 62 into place. In an exemplary embodiment, the electrodes 62 can be mounted over the generally planar element 24 prior to the step 116 of forming an outer layer 26.

In one embodiment, the mounting step 124 comprises a substep 126 of providing an electrical conductor or wire 64 associated with electrode 62 within at least one of the plurality of ribs 48 of the generally planar element 24. In accordance with some embodiments of the disclosure, the electrical conductor or wire 64 can be provided within the corresponding lumen 50 of at least one of the plurality of ribs 48 of the generally planar element 24. The corresponding lumen 50 can extend at least from the proximal end 14 of the shaft 12 to a location on the shaft 12 near where the electrode 62 is mounted. In accordance with other embodiments of the disclosure, the electrical conductors or wires 64 associated with electrodes 62 can be built into the walls of the longitudinally extending ribs 48 in order to reduce the risk of collapse of the corresponding lumen 50 of the ribs 48. In an exemplary embodiment, the substep 126 is performed prior to the step 116 of forming an outer layer 26. The substep 126 can be performed for each electrode 62 being mounted to the shaft 12. In an exemplary embodiment, the substep 126 comprises creating a small opening or aperture 66 on an outer radial surface of rib 48 at the location at which the electrode 62 is to be mounted to the shaft. The electrical conductor or wire 64 extends down the longitudinally extending rib 48 or the corresponding lumen 50 of the rib 48 to the proximal end thereof, where the electrical conductor or wire 64 can be coupled to an interconnect or connector, such as for example, the interconnect described above. The electrode 62 is put into place on the shaft 12 and covers and seals the access hole 66 through which the electrical conductor or wire 64 was extracted. This process is repeated for each electrode 62 being mounted on the shaft. As described above, in an exemplary embodiment, once all of the electrodes are mounted to the shaft 12, the shaft 12 and the electrodes 62 are covered with a layer of polymeric material, such as, for example, a polymer tube, as part of the subset 116 of forming an outer layer.

The electrodes 62 can be covered with one or more layers of material, such as for example, polymeric material and/or heat shrink material. It can be desirable for the method to include a step of removing the material from the outer surface of the electrodes 62. This can be performed in a number of ways, such as and without limitation, laser ablating the material away from the surface of the electrodes 62. It will be appreciated by those having ordinary skill in the art, however, that other known processes or techniques can be used to remove the material, and those processes or techniques remain within the spirit and scope of the disclosure.

In accordance with another aspect of the present disclosure, the sheath 10 is part of a system 200 for performing one or more diagnostic or therapeutic medical procedures, such as, for example and without limitation, drug delivery, the pacing of the heart, pacer lead placement, tissue ablation, monitoring, recording, and/or mapping of ECG signals and other electrophysiological data, and the like. In addition to the sheath 10, the system 200 comprises, at least in part, a system 202 for visualization, mapping, and/or navigation of internal body structures and medical devices. In an exemplary embodiment, the system 202 includes an ECU 204 and a display device 206. In another exemplary embodiment, the display device 206 is separate and distinct from the system 200, but electrically connected to and configured for communication with the ECU 204.

As will be described in greater detail below, one purpose of the system 200 is to accurately determine the position and orientation of the sheath 10, and in certain embodiments, to accurately display the position and orientation of the sheath 10 for the user to see. Knowing the position and orientation of the sheath 10 is beneficial regardless of whether the sheath is manually controlled (i.e., by a physician or clinician) or controlled by an automated guidance system, such as, for example, a robotic-based or magnetic-based system. For example, in a robotic-based system, it is important to know the accurate position and orientation of the sheath 10 to minimize error and provide patient safety by preventing perforations to the cardiac tissue. In a magnetic-based systems, it is important for the physician/clinician operating the system to know the accurate location and orientation of, for example, the fulcrum of a catheter used with the sheath 10. This information allows the physician/clinician to direct the orientation of the sheath 10 to optimize the ability to locate the catheter precisely and take full advantage of the magnetic manipulation capability offered by magnetic-based systems.

Figure 16:
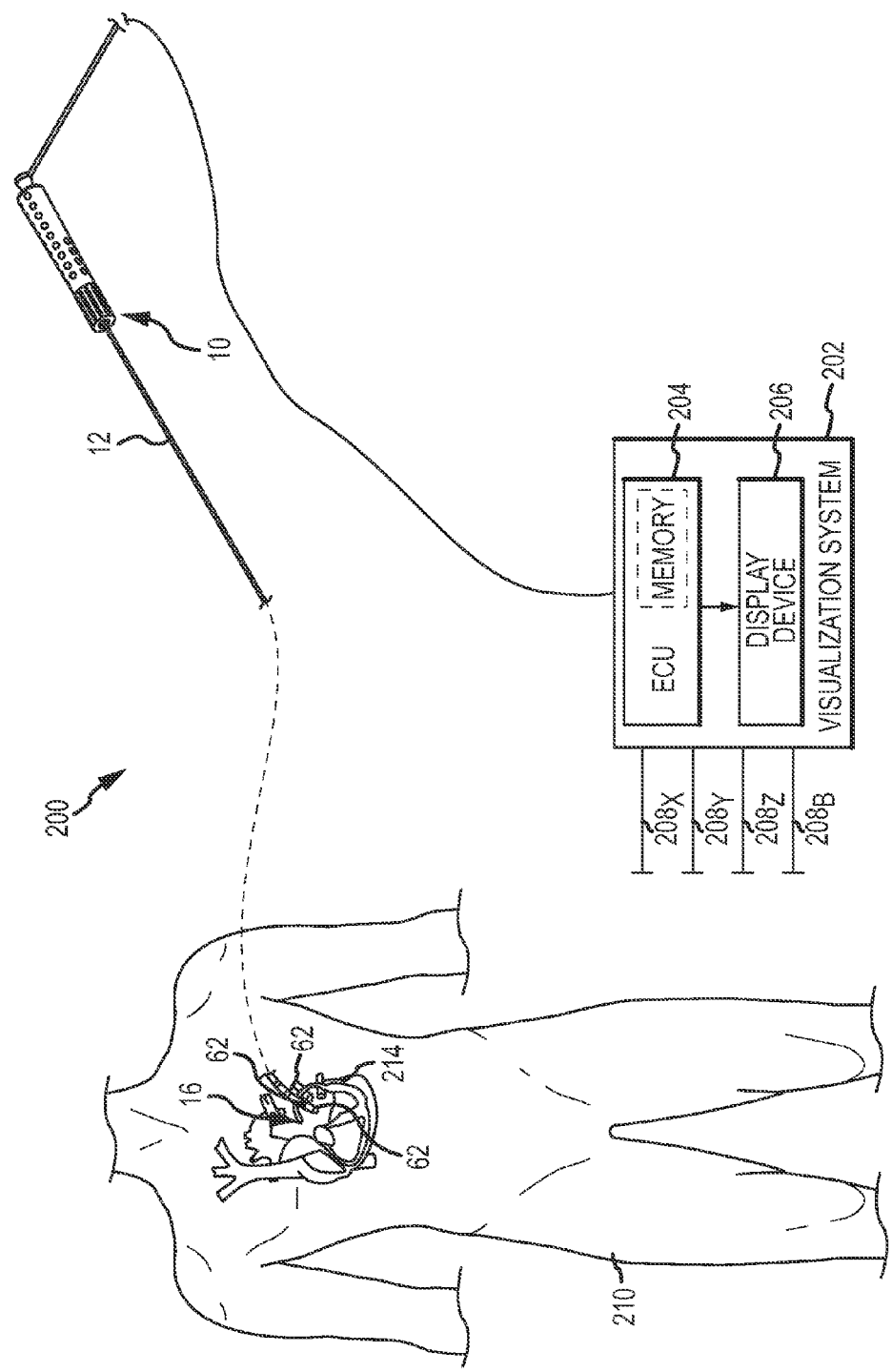
FIG. 16 is a diagrammatic view of a system for performing at least one of a diagnostic and a therapeutic medical procedure in accordance with present teachings.
Figure 17:
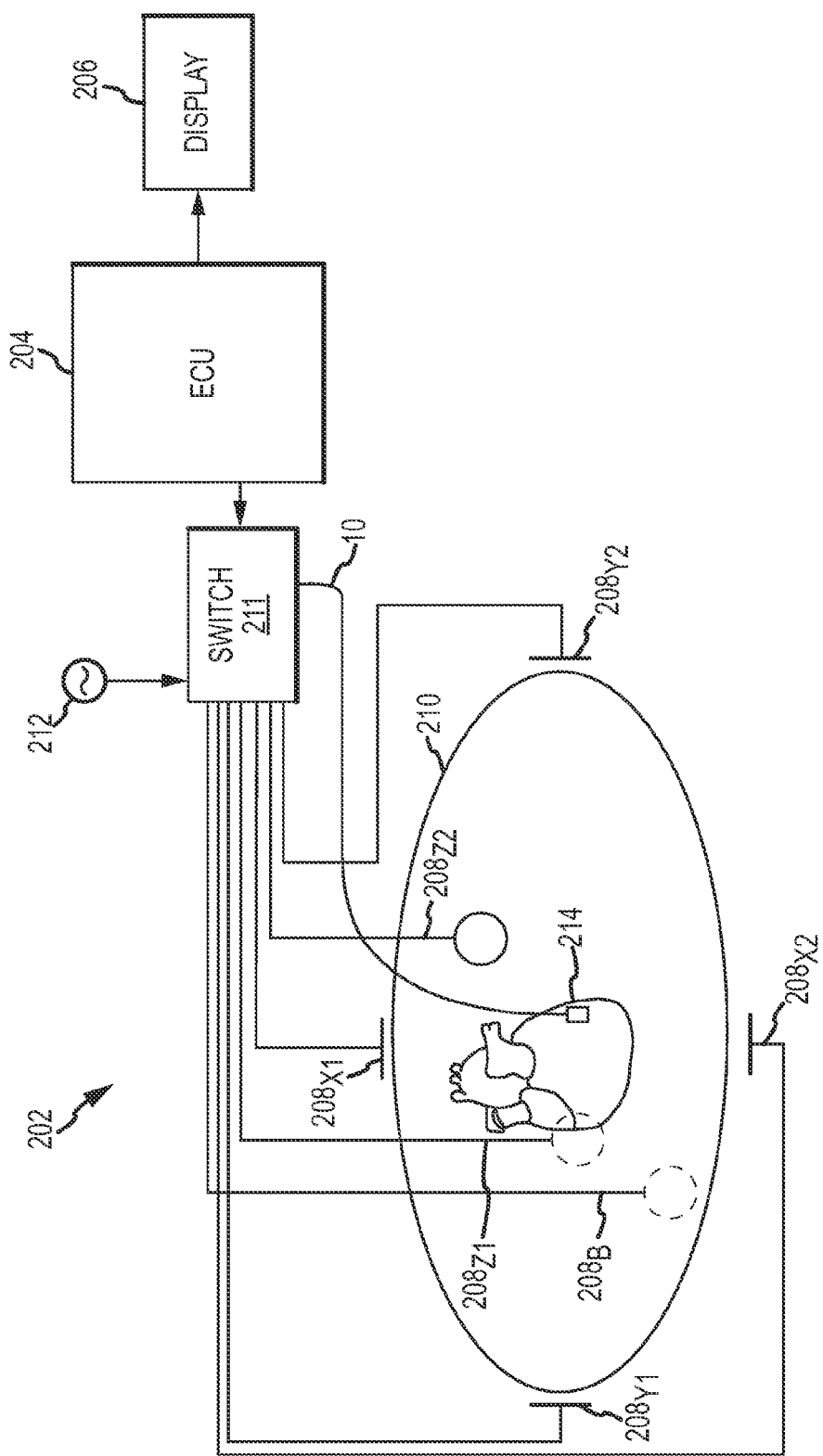
FIG. 17 is a simplified diagrammatic and schematic view of the visualization, navigation, and/or mapping system of the system illustrated in FIG. 16.

With reference to FIGS. 16 and 17, the visualization, navigation, and/or mapping system 202 will be described. The system 202 can comprise an electric field-based system, such as, for example, the ENSITE NAVX™ system commercially available from St. Jude Medical, Inc., and as generally shown with reference to U.S. Pat. No. 7,263,397 entitled "Method and Apparatus for Catheter Navigation and Location and Mapping in the Heart," the disclosure of which is incorporated herein by reference in its entirety. In other exemplary embodiments, however, the system 202 can comprise systems other than electric field-based systems. For example, the system 202 can comprise a magnetic field-based system such as the CARTO™ system commercially available from Biosense Webster, and as generally shown with reference to one or more of U.S. Pat. Nos. 6,498,944 entitled "Intrabody Measurement;" 6,788,967 entitled "Medical Diagnosis, Treatment and Imaging Systems;" and 6,690,963 entitled "System and Method for Determining the Location and Orientation of an Invasive Medical Instrument," the disclosures of which are incorporated herein by reference in their entireties. In another exemplary embodiment, the system 100 comprises a magnetic field-based system such as the gMPS system commercially available from MediGuide Ltd., and as generally shown with reference to one or more of U.S. Pat. Nos. 6,233,476 entitled "Medical Positioning System;" 7,197,354 entitled "System for Determining the Position and Orientation of a Catheter;" and 7,386,339 entitled "Medical Imaging and Navigation System," the disclosures of which are incorporated herein by reference in their entireties. In yet another embodiment, the system 202 can comprise a combination electric field-based and magnetic field-based system, such as, for example and without limitation, the CARTO 3™ system also commercially available from Biosense Webster, and as generally shown with reference to U.S. Pat. No. 7,536,218 entitled "Hybrid Magnetic-Based and Impedance Based Position Sensing," the disclosure of which is incorporated herein by reference in its entirety. In yet still other exemplary embodiments, the system 202 can comprise or be used in conjunction with other commonly available systems, such as, for example and without limitation, fluoroscopic, computed tomography (CT), and magnetic resonance imaging (MRI)-based systems. For purposes of clarity and illustration only, the system 202 will be described hereinafter as comprising an electric field-based system.

As illustrated in FIGS. 16 and 17, in addition to the ECU 204 and the display 206, in an exemplary embodiment the system 202 further comprises a plurality of patch electrodes 208. With the exception of the patch electrode 208B called a "belly patch," the patch electrodes 208 are provided to generate electrical signals used, for example, in determining the position and orientation of the sheath 10, and potentially in the guidance thereof. In one embodiment, the patch electrodes 208 are placed orthogonally on the surface of a patient's body 210 and used to create axes-specific electric fields within the body 210. For instance, in one exemplary embodiment, the patch electrodes $208x1$, $208x2$ can be placed along a first (x) axis. The patch electrodes $208y1$, $208y2$ can be placed along a second (y) axis. Finally, the patch electrodes $208z1$, $208z2$ can be placed along a third (z) axis. Each of the patch electrodes 208 can be coupled to a multiplex switch 211. In an exemplary embodiment, the ECU 204 is configured through appropriate software to provide control signals to switch 211 to thereby sequentially couple pairs of electrodes 208 to a signal generator 212. Excitation of each pair of electrodes 208 generates an electric field within the body 210 and within an area of interest such as, for example, heart tissue 214. Voltage levels at non-excited electrodes 208, which are referenced to the belly patch 208B, are filtered and converted, and provided to the ECU 204 for use as reference values.

As described above, the sheath 10 includes one or more electrodes 62 mounted thereon. In an exemplary embodiment, one of the electrodes 62 is a positioning electrode (however, in another exemplary embodiment, a plurality of the electrodes 62 are positioning electrodes). The positioning electrode 62 can comprise, for example and without limitation, a ring electrode or a magnetic coil sensor. The positioning electrode 62 is placed within electric fields created in the body 210 (e.g., within the heart) by exciting patch electrodes 208. The positioning electrode 62 experiences voltages that are dependent on the location between the patch electrodes 208 and the position of the positioning electrode 62 relative to the heart tissue 214. Voltage measurement comparisons made between the electrode 62 and the patch electrodes 208 can be used to determine the position of the positioning electrode 62 relative to the heart tissue 214. Movement of the positioning electrode 62 proximate the heart tissue 214 (e.g., within a heart chamber, for example) produces information regarding the geometry of the tissue 214. This information can be used, for example and without limitation, to generate models and maps of tissue or anatomical structures. Information received from the positioning electrode 62 (or if multiple positioning electrodes, the positioning electrodes 62) can be used to display on a display device, such as display device 206, the location and orientation of the positioning electrode 62 and/or the distal end of the sheath 10, and the shaft 12 thereof, in particular, relative to the tissue 214. Accordingly, among other things, the ECU 204 of the system 202 provides a means for generating display signals used to control the display device 206 and the creation of a GUI on the display device 206.

Accordingly, the ECU 204 can provide a means for determining the geometry of the tissue 214, EP characteristics of the tissue 214, and the position and orientation of the sheath 10. The ECU 204 can further provide a means for controlling various components of the system 202, including, without limitation, the switch 211. It should be noted that while in an exemplary embodiment the ECU 204 is configured to perform some or all of the functionality described above and below, in another exemplary embodiment, the ECU 204 can be a separate and distinct component from the system 202, and the system 202 can have another processor configured to perform some or all of the functionality (e.g., acquiring the position/location of the positioning electrode/sheath, for example). In such an embodiment, the processor of the system 202 would be electrically coupled to, and configured for communication with, the ECU 204. For purposes of clarity only, the description below will be limited to an embodiment wherein the ECU 204 is part of the system 202 and configured to perform all of the functionality described herein.

The ECU 204 can comprise a programmable microprocessor or microcontroller, or can comprise an application specific integrated circuit. The ECU 204 can include a central processing unit and an input/output interface through which the ECU 204 can receive a plurality of input signals including, for example, signals generated by patch electrodes 208 and the positioning electrode 62, and generate a plurality of output signals including, for example, those used to control and/or provide data to the display device 206 and the switch 211. The ECU 204 can be configured to perform various functions, such as those described in greater detail below, with appropriate programming instructions or code (i.e., software). Accordingly, the ECU 204 is programmed with one or more computer programs encoded on a computer storage medium for performing the functionality described herein.

In operation, the ECU 204 generates signals to control the switch 211 to thereby selectively energize the patch electrodes 208. The ECU 204 receives position signals (location information) from the sheath 10 (and particularly the positioning electrode 62) reflecting changes in voltage levels on the positioning electrode 62 and from the non-energized patch electrodes 208. The ECU 204 uses the raw location data produced by the patch electrodes 208 and positioning electrode 62 and corrects the data to account for respiration, cardiac activity, and other artifacts using known or hereinafter developed techniques. The ECU 204 can then generate display signals to create an image or representation of the sheath 10 that can be superimposed on an EP map of the tissue 214 generated or acquired by the ECU 204, or another image or model of the tissue 214 generated or acquired by the ECU 204.

In an embodiment wherein there are multiple positioning electrodes 62, the ECU 204 can be configured to receive positioning signals from two or more of the positioning electrodes 62, and to then create a representation of the profile of the distal portion of the sheath 10, for example, that can be superimposed onto an EP map of the tissue 214 generated or acquired by the ECU 204, or another image or model of the tissue 214 generated or acquired by the ECU 204.

One example where this functionality is valuable relates to the treatment of atrial fibrillation. In atrial fibrillation, often the left side of the heart has to be accessed. Using a technique called transseptal access, the physician uses a long, small diameter needle to pierce or puncture the heart's septal wall in an area known as the fossa ovalis to provide a means of access from the right atrium to the left atrium. Once transseptal access is obtained, physicians prefer not to lose it. However, for a variety of reasons, there are times when the access to the left side through the fossa ovalis is lost. As a result, the procedure time is increased and additional piercing or puncturing of the septal wall can be required.

If multiple positioning electrodes are mounted on the sheath, however, using the system 202 the location of the positioning electrodes 62, and therefore, the sheath 10 can be determined, and a shadow representation of the sheath 10 can be superimposed onto an image or model of the tissue 214 showing its position across the fossa ovalis. This gives the physician a reference to use as guidance, and more particularly, permits the physician to reposition the sheath 10 in the same location as the shadow representation, should access to the left side be lost during the procedure. Thus, additional piercing or puncturing of the septal wall can be avoided, the speed of the procedure will be reduced, and fluoroscopy time can also be reduced. Further, the positioning electrodes 62 can be used in real time to "straddle" the fossa ovalis so as to allow the physician to try to prevent the sheath 10 from coming out of the fossa ovalis in the first place.

Figure 18:
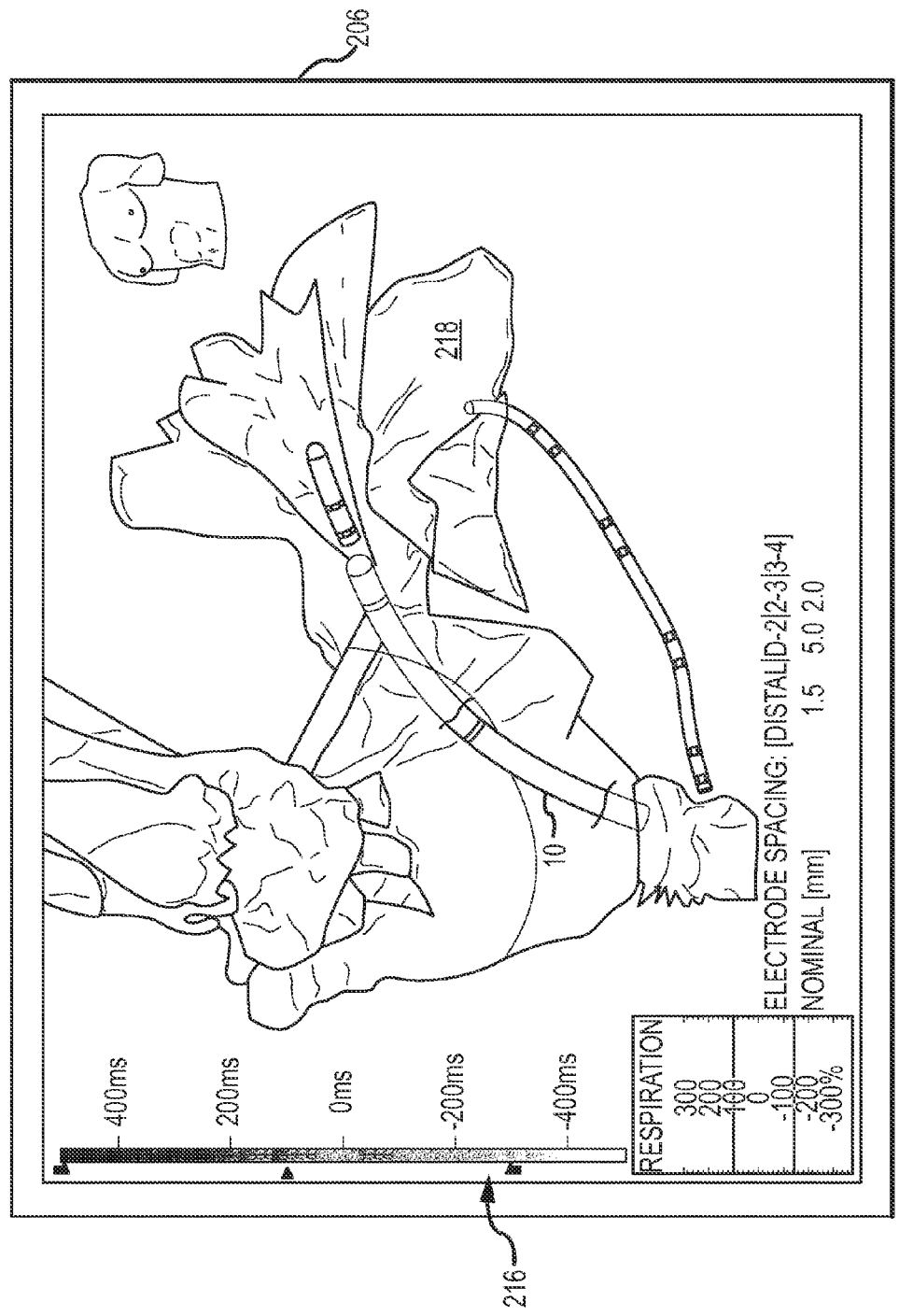
FIG. 18 is an exemplary embodiment of a display device of the system illustrated in FIG. 16 with a graphical user interface (GUI) displayed thereon.

With reference to FIGS. 16 and 18, the display device 206, which, as described above, can be part of the system 202 or a separate and distinct component, is provided to convey information to a clinician to assist in, for example, the performance of therapeutic or diagnostic procedures on the tissue 214. The display device 206 can comprise a conventional computer monitor or other display device known in the art. With particular reference to FIG. 18, the display device 206 presents a GUI 216 to the clinician. The GUI 216 can include a variety of information including, for example and without limitation, an image or model of the geometry of the tissue 214, EP data associated with the tissue 214, electrocardiograms, electrocardiographic maps, and images or representations of the sheath 10 and/or positioning electrode 62. Some or all of this information can be displayed separately (i.e., on separate screens), or simultaneously on the same screen. The GUI 216 can further provide a means by which a clinician can input information or selections relating to various features of the system 202 into the ECU 204.

The image or model of the geometry of the tissue 214 (e.g., image/model 218 shown in FIG. 18) can comprise a two-dimensional image of the tissue 214 (e.g., a cross-section of the heart) or a three-dimensional image of the tissue 214. The image or model 218 can be generated by the ECU 204 of the system 202, or alternatively, can be generated by another imaging, modeling, or visualization system (e.g., fluoroscopic, CT, MRI, etc. based systems) that are communicated to, and therefore, acquired by, the ECU 204. As briefly mentioned above, the display device 206 can also include an image or representation of the sheath 10 and/or the positioning electrode 62 illustrating their position and orientation relative to the tissue 214. The image or representation of the sheath 10 can be part of the image 218 itself (as is the case when, for example, a fluoroscopic system is used) or can be superimposed onto the image/model 218.

It will be appreciated that as briefly described above, in an exemplary embodiment, one or more of the electrodes 62 mounted on the shaft 12 can be used for purposes other than for determining positioning information. For example, one or more electrodes 62 can be used for pacing in the atrium of the heart to, for example, determine bi-directional block on the septal wall.

In addition, or alternatively, one or more of the electrodes 62 can be used for monitoring ECGs or to collect EP data in one or more areas in the heart. The information or data represented by the signals acquired by these electrodes 62 can be stored by the ECU 204 (e.g., in a memory of the device, for example), and/or the ECU 204 can display the data on an EP map or another image/model generated or acquired by the ECU 204, or otherwise display the data represented by the signals acquired by the electrodes 62 on a display device such as, for example, the display device 206. For example, in an exemplary embodiment, one or more electrodes 62 can be positioned such that as a therapeutic procedure is being performed on the left side of the fossa ovalis, ECGs or other EP data can be monitored on both the left and right sides of the fossa ovalis using the electrodes 62. One benefit of such an arrangement is that fewer medical devices need to be used during a procedure.

Accordingly, the system 200, and the visualization, navigation, and/or mapping system 202 thereof, in particular, is configured to carry out and perform any number of different functions, all of which remain within the spirit and scope of the present disclosure. It should be understood that the system 200, and particularly the ECU 204 as described above, can include conventional processing apparatus known in the art, capable of executing pre-programmed instructions stored in an associated memory, all performing in accordance with the functionality described herein. It is contemplated that the methods described herein, including without limitation the method steps of the embodiments of the disclosure, will be programmed in a preferred embodiment, with the resulting software being stored in an associated memory and where so described, can also constitute the means for performing such methods. Implementation of the disclosure, in software, in view of the foregoing enabling description, would require no more than routine application of programming skills by one of ordinary skill in the art. Such a system can be of the type having both ROM, RAM, a combination of non-volatile and volatile (modifiable) memory so that the software can be stored and yet allow storage and processing of dynamically produced data and/or signals.

Although only certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

What is claimed is:

1. A deflectable medical device, comprising:
   a shaft having a proximal end, a distal end, and a major lumen disposed therein extending between the proximal end and the distal end and configured to receive a second medical device therein, the shaft further comprising:
   an inner liner having an inner surface and an outer surface, the inner surface forming the major lumen;
   a generally planar element wrapped in a spiral pattern about the outer surface of the inner liner, wherein the generally planar element has a longitudinal axis and a plurality of longitudinally extending ribs and comprises a polymeric material;
   an outer layer comprising a polymeric material, wherein at least a portion of the outer layer is adjacent the outer surface of the inner liner; and,
   an electrode mounted on the outer layer of the shaft, wherein an electrical wire connected to the electrode is disposed within one of the plurality of ribs of the generally planar element
   wherein the inner liner has a plurality of minor lumens disposed therein.

2. The medical device of claim 1 further comprising means for deflecting the shaft in at least one direction relative to a longitudinal axis of the shaft, wherein the means for deflecting the shaft are at least partially disposed within at least one of the plurality of minor lumens.

3. The medical device of claim 1 wherein the polymeric material of the generally planar element comprises polyether ether ketone (PEEK), nylon, polytetrafluoroethylene (PTFE), or a combination thereof.

4. The medical device of claim 1 wherein each of the ribs has a corresponding lumen disposed therein.

5. The medical device of claim 4 wherein the electrical wire connected to the electrode is disposed within a corresponding lumen of the one rib of the generally planar element, the corresponding lumen extending at least from the proximal end of the shaft to a location on the shaft near where the electrode is mounted.

6. The medical device of claim 1 wherein the outer layer is bonded to the outer surface of the inner liner.

7. A system for performing a medical procedure, comprising:
   a first deflectable medical device having an elongate shaft and at least one electrode mounted on the shaft, the shaft comprising a proximal end, a distal end, and a major lumen extending between the proximal end and the distal end and configured to receive a second medical device therein, the elongate shaft further comprising:
   an inner liner having an inner surface and an outer surface, the inner surface forming the major lumen;
   a generally planar element having a longitudinal axis and having a plurality of longitudinally extending ribs, wherein the generally planar element comprises a polymeric material and is wrapped in a spiral pattern about the outer surface of the inner liner and wherein each of the ribs has a corresponding lumen disposed therein, an electrical wire connected to the at least one electrode disposed within the lumen of one of said plurality of longitudinally extending ribs;

an outer layer comprising a polymeric material, wherein at least a portion of the outer layer is adjacent the outer surface of the inner liner and wherein the at least one electrode is mounted on the outer layer; and an electronic control unit (ECU) configured to receive signals from the at least one electrode and, in response to the received signals, automatically perform at least one of:

determining a position of the at least one electrode; or monitoring electrophysiological data wherein the inner liner has a plurality of minor lumens disposed therein.

8. The system of claim 7 further comprising means for deflecting the shaft in at least one direction relative to a longitudinal axis of the shaft, wherein the means for deflecting the shaft are at least partially disposed within at least one of the plurality of minor lumens.

9. The system of claim 7 wherein the polymeric material of the generally planar element comprises polyether ether ketone (PEEK), nylon, polytetrafluoroethylene (PTFE), or a combination thereof.

10. A deflectable medical device, comprising:

a shaft having a proximal end, a distal end, and a major lumen disposed therein extending between the proximal end and the distal end and configured to receive a second medical device therein, the shaft further comprising:

an inner liner having an inner surface and an outer surface, the inner surface forming the major lumen;

a generally planar element wrapped in a spiral pattern about the outer surface of the inner liner, wherein the generally planar element has a longitudinal axis and a plurality of longitudinally extending ribs and comprises a polymeric material;

an outer layer comprising a polymeric material, wherein at least a portion of the outer layer is adjacent the outer surface of the inner liner; and, an electrode mounted on the outer layer of the shaft, wherein an electrical wire connected to the electrode is disposed within one of the plurality of ribs of the generally planar element wherein the planar element includes an aperture extending between the outer surface of the inner liner and the outer layer.

11. The medical device of claim 10 wherein the aperture is disposed between first and second ribs of the plurality of longitudinally extending ribs.

12. The medical device of claim 10 wherein the outer layer extends through the aperture to engage the inner liner.

13. A system for performing a medical procedure, comprising:

a first deflectable medical device having an elongate shaft and at least one electrode mounted on the shaft, the shaft comprising a proximal end, a distal end, and a major lumen extending between the proximal end and the distal end and configured to receive a second medical device therein, the elongate shaft further comprising:

an inner liner having an inner surface and an outer surface, the inner surface forming the major lumen;

a generally planar element having a longitudinal axis and having a plurality of longitudinally extending ribs, wherein the generally planar element comprises a polymeric material and is wrapped in a spiral pattern about the outer surface of the inner liner and wherein each of the ribs has a corresponding lumen disposed therein, an electrical wire connected to the at least one electrode disposed within the lumen of one of said plurality of longitudinally extending ribs;

an outer layer comprising a polymeric material, wherein at least a portion of the outer layer is adjacent the outer surface of the inner liner and wherein the at least one electrode is mounted on the outer layer; and an electronic control unit (ECU) configured to receive signals from the at least one electrode and, in response to the received signals, automatically perform at least one of:

determining a position of the at least one electrode; or monitoring electrophysiological data wherein the planar element includes an aperture extending between the outer surface of the inner liner and the outer layer.

14. The system of claim 13 wherein the aperture is disposed between first and second ribs of the plurality of longitudinally extending ribs.

15. The system of claim 13 wherein the outer layer extends through the aperture to engage the inner liner.

* * * * *